US010858401B2

(12) United States Patent
Moonen et al.

(10) Patent No.: US 10,858,401 B2
(45) Date of Patent: Dec. 8, 2020

(54) PYOLYSIN METHODS AND COMPOSITIONS

(71) Applicant: Zoetis Services LLC, Parsippany, NJ (US)

(72) Inventors: Glenn Andrew Moonen, Parkville (AU); George Moutafis, Parkville (AU); Allen Poppe, Lincoln, NE (US); John Herberg, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 15/557,592

(22) PCT Filed: Mar. 14, 2016

(86) PCT No.: PCT/US2016/022297
§ 371 (c)(1),
(2) Date: Sep. 12, 2017

(87) PCT Pub. No.: WO2016/145432
PCT Pub. Date: Sep. 15, 2016

(65) Prior Publication Data

US 2018/0057543 A1 Mar. 1, 2018

Related U.S. Application Data

(60) Provisional application No. 62/132,050, filed on Mar. 12, 2015.

(51) Int. Cl.

| | |
|---|---|
| ***A61K 39/02*** | (2006.01) |
| ***C07K 14/195*** | (2006.01) |
| ***C12N 1/20*** | (2006.01) |
| ***C12P 21/00*** | (2006.01) |
| ***A61K 39/00*** | (2006.01) |

(52) U.S. Cl.
CPC .............. *C07K 14/195* (2013.01); *C12N 1/20* (2013.01); *C12P 21/00* (2013.01); *A61K 2039/552* (2013.01)

(58) Field of Classification Search
USPC .................................................. 424/234, 100
See application file for complete search history.

(56) References Cited

FOREIGN PATENT DOCUMENTS

WO WO 2014/084964 A1 6/2014

OTHER PUBLICATIONS

Ding et al. J. Vet. Med. B 43, 179-188 , 1996 (Year: 1996).*
Funk et al. Veterinary Microbiology 50, pp. 129-142, 1996. (Year: 1996).*
Hague et al. Journal of Bacteriology , vol. 88, No. 5 pp. 1304-1309 , 1964.*
Machado, V. S. et al., Mar. 2014, Subcutaneous Immunization with Inactivated Bacterial Components and Purified Protein of *Escherichia coli*, Fusobacterium necrophorum and Trueperella pyogenes Prevents Puerperal Metritis in Holstein Dairy Cows, Plos One, vol. 9, e91734.
Amos, M. R. et al., 2014, "Differential Endometrial Cell Sensitivity to a Cholesterol-Dependent Cytolysin Links Trueperella pyogenes to Uterine Disease in Cattle", Biology of Reproduction, vol. 90, pp. 1-13.
PCT International Search Report and Written Opinion, International Application No. PCT/US2016/021529, International filing date Mar. 9, 2016, dated Jun. 9, 2016.

* cited by examiner

*Primary Examiner* — Jana A Hines
*Assistant Examiner* — Khatol S Shahnan Shah
(74) *Attorney, Agent, or Firm* — Vyacheslav Vasilyev

(57) ABSTRACT

Methods for improved cultivation media and culture conditions for *Trueperella pyogenes* are disclosed herein. Also disclosed are improved methods for the isolation and purification of pyolysin from *Trueperella pyogenes*.

16 Claims, 7 Drawing Sheets

PYOLYSIN METHODS AND COMPOSITIONS

CROSS-REFERENCED TO RELATED APPLICATIONS

This application is a national stage of PCT application PCT/US2016/022297 filed on Mar. 14, 2016, which in turn claims priority under 35 U.S.C § 119 to Provisional Patent Application Ser. No. 62/132,050 filed Mar. 12, 2015, herein incorporated by reference in their entirety.

FIELD OF THE INVENTION

The present invention relates for methods of increasing the amount of pyolysin produced by *Trueperella pyogenes*, a causative agent of bovine metritis. The invention further relates to compositions comprising pyolysin, isolated and purified using the methods described herein, and useful for reducing or preventing bovine metritis.

BACKGROUND

Metritis is the result of uterine infection in dairy cattle by various microbial pathogens. It usually develops following the onset of luteal function during the postpartum period. Bacteria normally found in the environment where livestock reside are presumably introduced into the uterus during or following calving. In postpartum cows that develop bacterial infections, the bacteria find their way into the uterus, but do not begin to proliferate immediately. Acute metritis occurs between day 0 and day 21 following parturition. Clinical endometritis (inflammation or irritation of the lining of the uterus, or endometrium) occurs between approximately day 21 and day 35 following parturition. Beyond day 35, endometritis often becomes subclinical.

There are multiple factors associated with natural infection, such as stress from calving, milk production/lactation, negative energy balance, immunosuppression, and the fact that such an animal is more susceptible to natural infection. One of the bacterial pathogens responsible for the onset of metritis and clinical endometritis is *Trueperella pyogenes*. This organism possesses a number of virulence factors that contribute to its pathogenic potential, one of which is pyolysin, a cholesterol-dependent cytolysin. This protein is a haemolysin, and is cytolytic for immune cells, including macrophages. Expression of pyolysin is required for virulence of this bacterium. This protein appears to be the most promising *T. pyogenes* subunit vaccine candidate identified to date. It is critical that isolated pyolysin be conformationally and immunologically similar/identical to the protein in its native state. Therefore, a method to produce, and if required, isolate native pyolysin from *T. pyogenes*, as well as an efficacious vaccine based on it, are highly desirable.

SUMMARY

Disclosed is a method for increasing the yield of pyolysin produced by *Trueperella pyogenes*, wherein the method comprises using a basal medium containing glucose, as well as an additional concentrated source of carbon selected from the group consisting of: glucose, galactose, sucrose, maltose, oligosaccharides, glycerol, lactose, dextran, dextrin, mono methyl succinate, and N-acetyl glucosamine; adding a chelating agent to the medium prior to the exhaustion of the glucose in the medium; harvesting *T. pyogenes*, and isolating pyolysin.

Disclosed is a method wherein the chelating agent is ethylene glycol tetraacetic acid (EGTA), ethylenediaminetetraacetic acid (EDTA), or a combination of the two.

Disclosed is a method for increasing the yield of pyolysin produced by *T. pyogenes*, wherein *T. pyogenes* replicates to a bacterial cell density higher than an optical density (O.D.) of 5 at 600 nm.

Disclosed is a method for increasing the yield of pyolysin produced by *T. pyogenes*, wherein the medium is maintained a temperature of between 28° C. and 32° C.

Disclosed is a method for increasing the yield of pyolysin produced by *T. pyogenes*, further comprising the use of a basal medium buffered with phosphate at a concentration of between 10 mM and 200 mM.

Disclosed is a method for increasing the yield of pyolysin produced by *T. pyogenes*, further comprising the use of a basal medium wherein the pH of the medium is between 6.0 and 8.0.

Disclosed is a method for increasing the yield of pyolysin produced by *T. pyogenes*, further comprising the use of a basal medium wherein the medium comprises hemin as an iron source.

Disclosed is a method for increasing the yield of pyolysin produced by *T. pyogenes*, further comprising the use of a basal medium comprising polysorbate 80.

Disclosed is a method for increasing the yield of pyolysin produced by *T. pyogenes*, further comprising the use of a basal medium comprising a vitamin solution.

Disclosed is a method for increasing the yield of pyolysin produced by *T. pyogenes*, wherein the vitamin solution comprises one or more of the following: Vitamin B12; myo-inositol; uracil nucleobase; nicotinic acid; calcium pantothenate; pyridoxal-HCl; pyridoxamine-2HCl; riboflavin; thiamine-HCl; p-aminobenzoic acid; biotin; folic acid; niacinamide; and 13-NAD.

Disclosed is a method for increasing the yield of pyolysin produced by *T. pyogenes*, wherein the vitamin solution comprises only pyridoxal-HCl.

Disclosed is a method for increasing the yield of pyolysin produced by *T. pyogenes*, comprising continuous, semi-continuous, or a one time supplementation with a concentrated carbon source.

Disclosed is a method for increasing the yield of pyolysin produced by *T. pyogenes*, comprising allowing the culture pH to decrease from the initial basal medium starting pH to a level between 5.50 and 6.50 and then controlling the pH between 5.50 and 6.50 by automatic addition of a basic titrant.

Disclosed is a method for increasing the yield of pyolysin produced by *T. pyogenes*, comprising separating the *T. pyogenes* proteases from the pyolysin.

Disclosed is a method for increasing the yield of pyolysin produced by *T. pyogenes*, wherein the separation of *T. pyogenes* proteases from pyolysin is achieved by a chromatography step.

Disclosed is a method for inactivating pyolysin, the method comprising adding formalin to a final concentration of between 0.1% and 0.5%.

Disclosed are immunogenic compositions useful for the vaccination of a bovine, particularly during the dry period, for the reduction or prevention of metritis.

Disclosed are immunogenic compositions comprising pyolysin, isolated from *T. pyogenes* grown in the media described herein.

Disclosed are immunogenic compositions comprising pyolysin, obtained by any of the methods described herein.

Disclosed are immunogenic compositions comprising pyolysin, obtained by any of the methods described herein, and a carrier.

Disclosed are immunogenic compositions comprising pyolysin, obtained by any of the methods described herein, and an adjuvant.

DESCRIPTION

Figure 1:
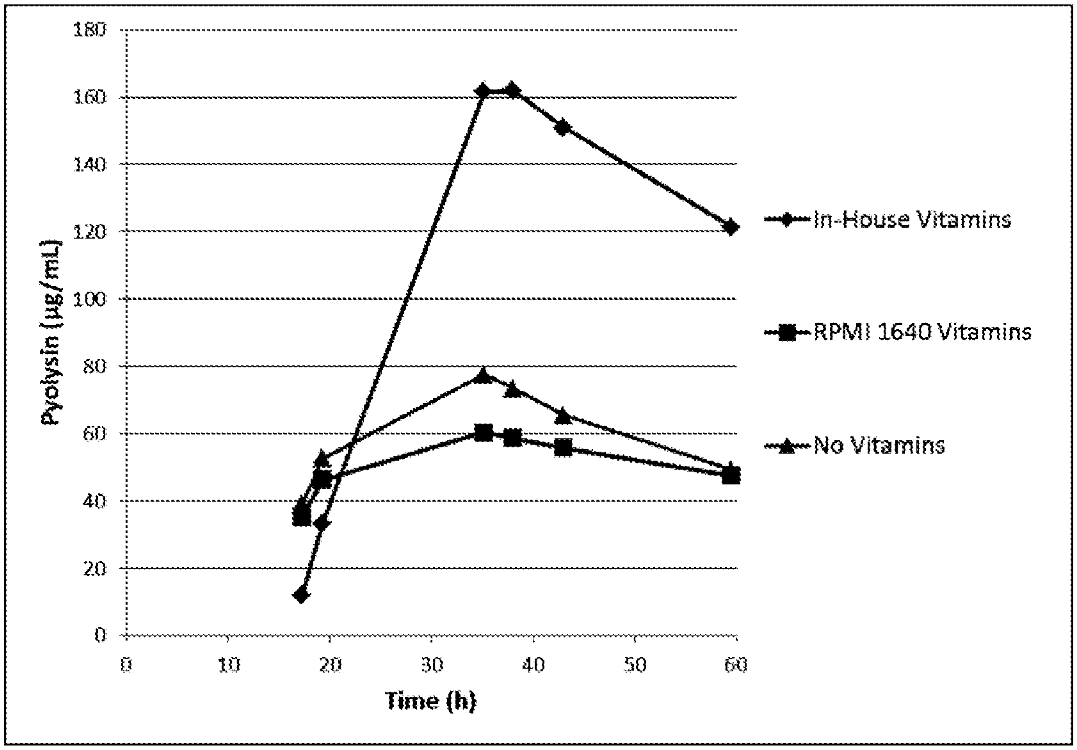
FIG. 1 is a comparison of the level of pyolysin production by *Trueperella pyogenes* in medium which contains no vitamins, an in-house vitamin solution, or a commercial vitamin solution.

All publications, patent applications, patents, and other references mentioned herein are incorporated by reference in their entirety.

The following definitions may be applied to terms employed in the description of the embodiments. The following definitions supersede any contradictory definitions contained in each individual reference incorporated herein by reference.

Unless otherwise defined herein, scientific and technical terms used in connection with the present embodiments shall have the meanings that are commonly understood by those of ordinary skill in the art. Further, unless otherwise required by context, singular terms shall include pluralities, and plural terms shall include the singular.

The terms "about", "approximately", and the like, as used herein, when used in connection with a measurable numerical variable, mean the indicated value of the variable, and all values of the variable that are within the experimental error of the indicated value (e.g., within the 95% confidence interval for the mean), or within 10 percent of the indicated value, whichever is greater. In terms of days, "about" is construed to mean plus or minus 1 day; e.g. "about 3 days" can mean 2, 3 or 4 days.

The term "animal", as used herein, means any animal that is susceptible to endometritis, including mammals, both domesticated and wild. Preferably, "animal", as used herein, refers to a bovine.

The terms "bacteria", "bacterial species", "bacterium", and the like, as used herein, mean a large domain of prokaryotic microorganisms. Preferably, "bacteria", as used herein, refer to microorganisms including *Trueperella pyogenes* and related bacteria.

The term "bacterial cell density", as used herein, means the number of bacteria present in a culture. One method of quantifying the number of bacteria is by measuring the optical density of a culture in a spectrophotometer, typically at 600 nm.

The term "basal medium", as used herein, means the medium into which a microorganism is initially inoculated. No replication of the microorganism has yet taken place, which could have an effect on the pH and/or concentration of various media components.

The term "bovine", as used herein, means a diverse group of medium- to large-sized ungulates, generally having cloven hoofs, and at least one of the sexes having true horns. Bovines include, but are not limited to, domestic cattle, bison, African buffalo, water buffalo, yak, and four-horned or spiral-horned antelope.

The terms "culture" or "culture medium", as used herein, mean the medium containing a microorganism.

The term "dry period", as used herein, means the period during which no milking occurs in a cow; this period is to prepare the cow and her udder for the next lactation.

The term "endometritis", as used herein, means an inflammation or irritation of the inner lining of the uterus, also referred to as the "endometrium".

The term "glucose exhaustion", as used herein, means the consumption, metabolism, or breaking down of most or all of the available glucose in a culture. For example, "exhaustion" may be when the concentration of the carbon source is at or below 10 mM.

The terms "gonadotropin-releasing hormone", "GnRH", "luteinizing hormone-releasing hormone", "LHRH", and the like, as used herein, mean a peptide hormone responsible for the synthesis and secretion from the anterior pituitary of the gonadotropins, follicle-stimulating hormone (FSH) and luteinizing hormone (LH). GnRH secretion is pulsatile in all vertebrates, and is necessary for correct reproductive function.

The term "inoculum", as used herein, means an amount or culture of a microorganism. Preferably "inoculum" refers to an amount of a bacterial culture.

The terms "intramuscular", "intramuscularly", and the like, as used herein, mean injection of a substance into a muscle.

The term "irritation", as used herein, means a condition or reaction to a stimulus or agent which causes damage to the cells on the surface of a tissue.

The terms "lactate", "lactating", and "lactation", as used herein, mean the secretion of milk from the mammary glands, and the period of time that a female produces milk to feed her young.

The term "parturition", as used herein, means the time when a bovine gives birth to a calf.

The terms "pathogenic microorganism" or "pathogen", as used herein, mean a microbe capable of causing disease or a pathological condition in an animal. Such can include, but are not limited to, a bacterium, virus, fungus, or yeast.

The terms "pregnant" or "pregnancy", as used herein, mean the fertilization and development of one or more offspring, known as an embryo or fetus, in a female's uterus.

The term "progesterone", as used herein, means a steroid hormone involved in the estrous cycle, pregnancy and embryogenesis of animals. Progesterone belongs to a class of hormones called progestogens.

The terms "uterus", "uterine" and the like, as used herein, mean the female hormone-responsive reproductive organ of most mammals that nourishes the embryo and fetus during pregnancy.

The terms "veterinarily-acceptable carrier" or "carrier", as used herein, refers to substances which are, within the scope of sound medical judgment, suitable for use in contact with the tissues of animals, without undue toxicity, irritation, allergic response, and the like, commensurate with a reasonable benefit-to-risk ratio, and effective for their intended use.

The following description is provided to aid those skilled in the art in practicing the present invention. Even so, this description should not be construed to unduly limit the present invention, as modifications and variations in the embodiments discussed herein can be made by those of ordinary skill in the art, without departing from the spirit or scope of the present inventive discovery.

Cultivation Techniques

Bacteria, including *Trueperella pyogenes*, can be grown in a vessel containing growth medium that will allow for replication of the bacteria to high numbers, facilitating isolation of the desired protein(s). The growth medium can be in the form of a nutrient broth, and can contain any number of various ingredients serving as sources for various compounds and components necessary or useful for growth. This includes a source(s) for nutrients. The nutrient components of culture media are carefully selected, and can include proteins, peptides and amino acids. These components can serve as carbon and nitrogen sources for the bacteria. More demanding organisms may require the addition of supplemental nutrient sources.

An energy source is also critical in the growth medium. It is often supplied in the form of a carbohydrate. The most common substance added to culture media as a source of energy to increase the rate of growth of organisms is glucose. Other carbohydrates may also be used or required. Alternate carbon sources may include, but not be limited to, galactose, various disaccharides, such as sucrose, lactose or maltose, and oligosaccharides. Other carbon sources can also include glycerol, dextran, dextrin, mono methyl succinate, and N-acetyl glucosamine.

Essential metals and minerals may also be added in the medium. These inorganic components of culture media can include macro-components, such as Na, K, Cl, P, S, Ca, Mg, and Fe. Various micro-components may also be required, such as Zn, Mn, Br, B, Cu, Co, Mo, V, and Sr. $PO_4$ may also be required in the medium. It can be present at a concentration of between 10 mM and 200 mM, including 10, 15, 20, 25, 30, 35, 40, 45, 50, 55, 60, 65, 70, 75, 80, 85, 90, 95, 100, 105, 110, 115, 120 125, 130, 135, 140, 145, 150, 155, 160, 165, 170, 175, 180, 185, 190, 195, and 200 mM.

It is also important that the pH of a culture medium be maintained around the range necessary for growth of the desired bacteria. The pH of the culture medium can be between 6.0 and 8.0, including 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 and 8.0. The use of buffer compounds at specific pK values is especially important when fermentable carbohydrates are added as energy sources. Phosphates, acetates, citrates, zwitterionic compounds, and specific amino acids are examples of buffering agents that may be added to culture media. One potential side effect of such compounds is their ability to chelate (or bind) divalent cations (e.g., Ca++ and Mg++). The effect of these binding or chelating agents may be seen in diminished growth or failure to grow at all, unless care is taken to supplement the essential cations in the formulation. pH can also be regulated by the addition of various acidic or basic solutions, such as sodium bicarbonate and sodium hydroxide. Dissolved $CO_2$ can also be used to adjust the pH of a culture.

The growth medium can also contain colored indicator substances, which can serve as an effective way of detecting fermentation of specific carbohydrates in a culture medium. Such compounds should change color distinctly and rapidly at critical pH values. Most of these compounds used—such as phenol red, bromocresol purple, and fuchsin—can be toxic; therefore, it is essential to use low concentrations of them.

Selective agents may also be necessary in the growth medium. Chemicals or antimicrobials are added to culture media to make it selective for certain microorganisms. The selective agents are chosen and added at specific concentrations to suppress the growth of unwanted organisms, or to enhance the growth of desired organisms, in a polymicrobial sample. It is essential to establish that the selective agents will not only inhibit the unwanted organisms, but will also allow uninhibited growth of the desired organisms.

Gelling agents can also be useful in growth media. The most common gel-forming substance used in culture media is agar. Agar is obtained from agarophyte seaweeds, mainly *Gelidium, Gracilaria* and *Pterocladia* species. It is extracted as an aqueous solution at greater than 100° C., decolourised, filtered, dried, and milled to a powder. Agar is not an inert gelling agent, and can contribute nutrients and/or toxic agents to culture media, depending on the chemical processes used in its production.

Other components can also be added to growth media, serving a specific purpose. These can include various growth factors, whole blood or blood components, and hormones.

The temperature at which the culture medium is maintained is an important factor with regards to the amount of toxin produced. In order to maximize the amount of toxin produced, the temperature of the medium can be maintained at 37° C. or lower. Preferably, the temperature can be maintained at between 21° C. and 36° C. More preferably, the temperature can be maintained at between 25° C. and 34° C. Most preferably, the temperature can be maintained at between 28° C. and 32° C.

Protein Purification Techniques

Various preparative methods of protein purification are contemplated herein. Such methods are aimed at recovering relatively large quantities of purified protein(s) for subsequent use, including for the preparation of immunogenic compositions. (Analytical purification methods are more for the production of small amounts of proteins for a variety of research or analytical purposes.) The major steps of preparative protein purification include extraction, purification, and if necessary, concentration.

In order to extract a protein, it may need to be brought into solution. This can be accomplished by breaking or disrupting the tissue or cells containing it. There are several methods to achieve this: repeated freezing and thawing, sonication, homogenization by high pressure, filtration, or permeabilization by organic solvents. The method of choice depends on how fragile the protein is, and how sturdy the cells are. Usually for most of the conventional purposes, column chromatography is used to achieve purification. After this extraction process, soluble proteins will be in the solvent, and can be separated from cell membranes, DNA, etc., by centrifugation.

It may be necessary, prior to or in conjunction with the extraction of a protein, to inhibit proteases which may be present and capable of degrading the protein(s) being purified. There are multiple classes of proteases which may be present, including serine proteases, cysteine proteases, metalloproteases, and aspartic proteases. Various methods are available for inhibiting the various classes of proteases, and can include, but not be limited to, the addition of other proteins which act to inhibit proteases, or various chemical compounds which may inhibit the activity of the proteases.

Purification strategies generally involve some type of chromatographic step(s) and equipment. A purification process generally utilizes three properties to separate proteins. First, proteins can be purified according to their isoelectric points, such as by running them through a pH-graded gel or an ion exchange column. Second, proteins can be separated according to their size or molecular weight, such as via size exclusion chromatography or by SDS-PAGE (sodium dodecyl sulfate-polyacrylamide gel electrophoresis). Third, proteins may be separated by polarity/hydrophobicity, such as by high performance liquid chromatography or reversed-phase chromatography. A protein purification protocol may contain one or more chromatographic steps. Other chromatographic methods also exist, including hydrophobic interaction chromatography (separating compounds based on surface hydrophobicity) and affinity chromatography (separation of compounds using various resins having specificity for the ligands attached to the compound).

Should concentration of the protein be necessary, this can be achieved using various techniques, which may include lyophilization (drying of a protein), and ultrafiltration (concentrating using selective permeable membranes).

Immunogenic Compositions

Immunogenic compositions of the present invention can be administered to animals to induce an effective immune response against *T. pyogenes*. Accordingly, the present invention provides methods of stimulating an effective immune response by administering to an animal a therapeutically effective amount of an immunogenic composition of the present invention described herein.

Pyolysin can be inactivated prior to its use in an immunogenic composition. Methods of inactivation can include, but are not limited to, heat treatment, UV light treatment, adjustment of pH (up or down), or treatment with various chemical agents. Such chemical agents can include, but are not limited to: reducing agents, such as dithiothreitol (DTT) or beta-mercaptoethanol (BME); detergents, such as sodium dodecyl sulfate (SDS), Triton X-100, or CHAPS; chaotropic agents, such as phenol or urea; and reactive disinfectants, such as formaldehyde or gluteraldehyde. Methods for the use of such methods and agents are readily accomplished using standard techniques well known to those skilled in the art.

Immunogenic compositions of the present invention can include one or more adjuvants. Adjuvants include, but are not limited to, the RIBI adjuvant system (Ribi Inc.; Hamilton, Mont.), alum, aluminum hydroxide gel, oil-in water emulsions, water-in-oil emulsions such as, e.g., Freund's complete and incomplete adjuvants, Block copolymer (CytRx; Atlanta, Ga.), SAF-M (Chiron; Emeryville, Calif.), AMPHIGEN® adjuvant, killed *Bordetella*, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), GPI-0100 (Galenica Pharmaceuticals, Inc.; Birmingham, Ala.) or other saponin fractions, monophosphoryl lipid A, avridine lipid-amine adjuvant, heat-labile enterotoxin from *Escherichia coli* (recombinant or otherwise), cholera toxin, or muramyl dipeptide. Also useful is MPL™ (3-O-deacylated monophosphoryl lipid A; Corixa, Hamilton, Mont.), which is described in U.S. Pat. No. 4,912,094, and hereby incorporated by reference. Also suitable for use as adjuvants are synthetic lipid A analogs or aminoalkyl glucosamine phosphate (AGP) compounds, or derivatives or analogs thereof, which are available from Corixa (Hamilton, Mont.), and which are described in U.S. Pat. No. 6,113,918, hereby incorporated by reference. A combination of Quil A and cholesterol can also be used as an adjuvant.

Synthetic polynucleotides, such as oligonucleotides containing CpG motifs (U.S. Pat. No. 6,207,646, hereby incorporated by reference), can also be used as adjuvants. CpG oligonucleotides, such as P-class immunostimulatory oligonucleotides, are useful, including E-modified P-class immunostimulatory oligonucleotides. Sterols can also be useful as adjuvants. Those suitable for use can include β-sitosterol, stigmasterol, ergosterol, ergocalciferol, and cholesterol. The adjuvant compositions can further include one or more polymers such as, for example, DEAE Dextran, polyethylene glycol, polyacrylic acid, and polymethacrylic acid (e.g., CARBOPOL®). The adjuvant compositions can further include one or more Th2 stimulants such as, for example, Bay R1005(R) and aluminum. The adjuvant compositions can further include one or more immunomodulatory agents, such as quaternary ammonium compounds (e.g., DDA), interleukins, interferons, or other cytokines.

A number of cytokines or lymphokines have been shown to have immune-modulating activity, and thus may be used as adjuvants. These can include, but not be limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (see, for example, U.S. Pat. No. 5,078,996, and ATCC Accession Number 39900), macrophage colony stimulating factor, granulocyte colony stimulating factor, GSF, and the tumor necrosis factors α and β. Still other adjuvants useful in this invention include chemokines, including without limitation, MCP-1, MIP-1α, MIP-1β, and RANTES. Adhesion molecules, such as a selectin, e.g., L-selectin, P-selectin, and E-selectin may also be useful as adjuvants. Still other useful adjuvants include, without limitation, a mucin-like molecule, e.g., CD34, GlyCAM-1 and MadCAM-1; a member of the integrin family such as LFA-1, VLA-1, Mac-1 and p150.95; a member of the immunoglobulin superfamily such as PECAM, ICAMs (e.g., ICAM-1, ICAM-2 and ICAM-3), CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE).

Cationic carriers can also be useful in adjuvant compositions. Suitable cationic carriers include, without limitations, dextran, dextran-DEAE (and derivatives thereof), PEG's, guar gums, chitosan derivatives, polycellulose derivatives like hydroxyethyl cellulose (HEC), polyethylenimene, poly aminos, like polylysine, and the like.

Immunogenic compositions of the present invention can be made in various forms, depending upon the route of administration. For example, the immunogenic compositions can be made in the form of sterile aqueous solutions or dispersions, suitable for injectable use, or made in lyophilized forms using freeze-drying techniques. Lyophilized immunogenic compositions are typically maintained at about 4° C., and can be reconstituted in a stabilizing solution, e.g., saline or HEPES, with or without adjuvant. Immunogenic compositions can also be made in the form of suspensions or emulsions.

These immunogenic compositions can contain additives suitable for administration via any conventional route of administration. The immunogenic compositions of the invention can be prepared for administration to subjects in the form of, for example, liquids, powders, aerosols, tablets, capsules, enteric-coated tablets or capsules, or suppositories. Thus, the immunogenic compositions may also be in the form of, but are not limited to, suspensions, solutions, emulsions in oily or aqueous vehicles, pastes, and implantable sustained-release or biodegradable formulations. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Other useful parenterally-administrable formulations include those which comprise the active ingredient in microcrystalline form, in a liposomal preparation, or as a component of a biodegradable polymer system. Compositions for sustained release or implantation may comprise pharmaceutically acceptable polymeric or hydrophobic materials, such as an emulsion, an ion exchange resin, a sparingly soluble polymer, or a sparingly soluble salt.

Immunogenic compositions generally comprise a veterinarily-acceptable carrier. Such carriers include, without limitation, water, saline, buffered saline, phosphate buffer, alcoholic/aqueous solutions, emulsions or suspensions. Other conventionally employed diluents, adjuvants, and excipients may be added in accordance with conventional techniques. Such carriers can include ethanol, polyols, and suitable mixtures thereof, vegetable oils, and injectable organic esters. Buffers and pH-adjusting agents may also be employed, and include, without limitation, salts prepared from an organic acid or base. Representative buffers include, without limitation, organic acid salts, such as salts of citric acid (e.g., citrates), ascorbic acid, gluconic acid, carbonic acid, tartaric acid, succinic acid, acetic acid, phthalic acid, Tris, trimethylamine hydrochloride, or phosphate buffers. Parenteral carriers can include sodium chloride solution, Ringer's dextrose, dextrose, trehalose, sucrose, lactated Ringer's, or fixed oils. Intravenous carriers can include fluid and nutrient replenishers, electrolyte replenishers, such as those based on Ringer's dextrose, and the like. Preservatives and other additives such as, for example, antimicrobials, antioxidants, chelating agents (e.g., EGTA; EDTA), inert gases, and the like may also be provided in the pharmaceutical carriers. The present invention is not limited by the selection of the carrier. The preparation of these pharmaceutically-acceptable compositions, from the above-described components, having appropriate pH, isotonicity, stability and other conventional characteristics, is within the skill of the art. See, e.g., texts such as Remington: The Science and Practice of Pharmacy, 20th ed, Lippincott Williams & Wilkins, pub., 2000; and The Handbook of Pharmaceutical Excipients, 4th edit., eds. R. C. Rowe et al, APhA Publications, 2003.

Recombinant Techniques

In yet other embodiments of the invention, the immunogenic composition may comprise a recombinant vaccine. Such recombinant vaccines could comprise a recombinant protein, or alternatively a vector and heterologous insert encoding for said recombinant protein. The heterologous inserts in some embodiments comprise one or more nucleic acid sequences encoding the proteins of the instant invention. The insert may optionally comprise a heterologous promoter, such as, for example, synthetic promoters known in the art. Alternatively, the promoters of the host vector may exert transcriptional control over the expression of the inserts. Suitable non-limiting examples of promoters—which may be native or heterologous, depending on the choice of the vector—are H6 vaccinia promoter, I3L vaccinia promoter, 42K poxviral promoter, 7.5K vaccinia promoter, and Pi vaccinia promoter.

In some embodiments, the vectors may be viral vectors, including, without limitations, vaccinia and pox virus vectors, such as parapox, racoonpox, swinepox, and different avipox vectors (e.g., canarypox and fowlpox strains). Generally, sequences that are non-essential for the viral host are suitable insertions sites for the inserts of the instant invention. The strains recited above are well-characterized in the art, and some insertions sites in these vectors are well known.

There are several known methods or techniques that can be used to clone and express the nucleotide sequences of the present invention. For example, the sequences can be isolated as restriction fragments, and cloned into cloning and/or expression vectors. The sequences can also be PCR-amplified, and cloned into cloning and/or expression vectors. Alternatively, they can be cloned by a combination of these two methods. Standard molecular biology techniques known in the art, and not specifically described, can be generally followed as described in Sambrook et al., *Molecular Cloning: A Laboratory Manual*, Cold Spring Harbor Laboratory Press, New York (1989); Ausubel et al., *Current Protocols in Molecular Biology*, John Wiley and Sons, Baltimore, Md. (1989); Perbal, *A Practical Guide to Molecular Cloning*, John Wiley & Sons, New York (1988); Watson et al., *Recombinant DNA*, Scientific American Books, New York; Birren et al (eds) *Genome Analysis: A Laboratory Manual Series, Vols.* 1-4 Cold Spring Harbor Laboratory Press, New York (1998); and methodology set forth in U.S. Pat. Nos. 4,666,828; 4,683,202; 4,801,531; 5,192,659 and 5,272,057. Polymerase chain reaction (PCR) is carried out generally as described in *PCR Protocols: A Guide to Methods and Applications*, Academic Press, San Diego, Calif. (1990).

The present invention encompasses the use of prokaryotic and eukaryotic expression systems, including vectors and host cells, which may be used to express both truncated and full-length forms of the recombinant polypeptides expressed by the nucleotide sequences of the present invention. A variety of host-expression vector systems may be utilized to express the polypeptides of the present invention. Such host-expression systems also represent vehicles by which the coding sequences of interest may be cloned, and the expressed protein(s) subsequently purified. The present invention further provides for host cells which may, when transformed or transfected with the appropriate vector or nucleotide sequence, express the encoded polypeptide gene product of the invention. Such host cells include, but are not limited to, microorganisms such as bacteria (e.g., *Escherichia coli, Bacillus subtilis*) transformed with recombinant bacteriophage DNA, plasmid DNA, or cosmid DNA expression vectors containing coding sequences; yeast (e.g., *Saccharomyces, Pichia*) transformed with recombinant yeast expression vectors containing the coding sequences; insect cell systems infected with recombinant virus expression vectors (e.g., baculovirus) containing the coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3) harboring recombinant expression constructs containing promoters derived from the genome of mammalian cells (e.g., metallothionein promoter), or from mammalian viruses (e.g., the adenovirus late promoter; the vaccinia virus 7.5K promoter), and the coding sequences.

The vectors of the invention can be derived from, but not limited to, bacterial plasmids, bacteriophage, yeast episomes, yeast chromosomal elements, mammalian viruses, mammalian chromosomes, and combinations thereof, such as those derived from plasmid and bacteriophage genetic elements including, but not limited to, cosmids and phagemids.

Vectors of the present invention can be used for the expression of polypeptides. Generally, the vectors of the invention include cis-acting regulatory regions, operably linked to the polynucleotide that encodes the polypeptides to be expressed. The regulatory regions may be constitutive or inducible. Appropriate trans-acting factors are supplied by the host by an in vitro translation system, by a complementing vector, or by the vector itself upon introduction into the host.

To facilitate isolation of pyolysin, a fusion polypeptide can be made, wherein the pyolysin is linked to a heterologous polypeptide, which enables isolation by affinity chromatography. Preferably, a fusion polypeptide is made using one of the expression systems known to those of skill in the art. For example, the polynucleotide encoding for the pyolysin is linked at either its 5' or 3' end to a nucleic acid encoding a heterologous polypeptide. The nucleic acids are linked in the proper codon reading frame, to enable production of a fusion polypeptide, wherein the amino and/or carboxyl terminus of the pyolysin is fused to a heterologous polypeptide, which allows for the simplified recovery of the antigen as a fusion polypeptide. The fusion polypeptide can also prevent the antigen from being degraded during purification. In some instances, it can be desirable to remove the heterologous polypeptide after purification. Therefore, it is also contemplated that the fusion polypeptide comprise a cleavage site at the junction between the pyolysin and the heterologous polypeptide. The cleavage site consists of an amino acid sequence that is cleaved with an enzyme specific for the amino acid sequence at the site. Examples of such cleavage sites that are contemplated include the enterokinase cleavage site (cleaved by enterokinase), the factor Xa cleavage site (cleaved by factor Xa), and the GENENASE cleavage site (cleaved by GENENASE; New England Biolabs; Beverly, Mass.).

An example of a prokaryote expression system for producing recombinant polypeptides for use in immunogenic compositions is the Glutathione S-transferase (GST) Gene Fusion System (Amersham Pharmacia Biotech; Piscataway, N.J.). Another method for producing the fusion protein is a method which links a DNA sequence encoding a polyhistidine tag in-frame with the DNA encoding the antigen. The tag allows for purification of the fusion polypeptide by metal affinity chromatography, preferably nickel affinity chromatography. The Xpress System (Invitrogen; Carlsbad, Calif.) is an example of a commercial kit available for making and then isolating polyhistidine-polypeptide fusion proteins. Also, the pMAL Fusion and Purification System (New England Biolabs; Beverly, Mass.) is another example of a method for making a fusion polypeptide, wherein a maltose binding protein (MBP) is fused to the antigen. The MBP facilitates isolation of the fusion polypeptide by amylose affinity chromatography. Other fusion partners, and methods for generating such fusions, are readily available, and known to those of skill in the art. These fusions can be used in their entirety as the immunogenic composition, or they can be cleaved at the junction between the recombinant antigen and the heterologous polypeptide.

The vectors of the invention can include any elements typically included in an expression or display vector, including, but not limited to, origin of replication sequences, one or more promoters, antibiotic resistance genes, leader or signal peptide sequences, various tag sequences, restriction sites, ribosome binding sites, translational enhancers (sequences capable of forming stem loop structures for mRNA stability post-transcription), sequences that encode amino acids lacking a stop codon, and sequences that encode a bacterial coat protein.

The present invention is further illustrated by, but by no means limited to, the following examples.

EXAMPLES

Example 1. Improved Method for the Expression, Isolation and Purification of Pyolysin The medium used for all fermentation stages was a heat-sterilized tryptone/yeast extract/Tween 80/glucose/phosphate/Hemin solution. A sterile filtered vitamin solution and further filter-sterilized glucose solution was added to the medium post heat sterilization. A frozen wild-type *Trueperella pyogenes* ampoule was thawed, and used to inoculate a flask (at ~30% fill volume) containing the medium (0.5% v/v); this was incubated for 16-28 hours, at 37° C., 100 rpm in a $CO_2$ incubator set at 5%. A second flask containing medium was then inoculated with 10% v/v of culture from the first flask; this was then incubated for 4 to 8 hours, again at 37° C., 100 rpm in a $CO_2$ incubator set at 5%. A fermenter was then inoculated with 0.5% v/v of culture from the second flask. The temperature was held at 37° C., and the starting pH was 7.2 to 7.4. The pH was allowed to drop to pH 6.15, and was then controlled in one direction only with 30% NaOH. Dissolved oxygen was maintained at 5% using pure oxygen at a maximum flowrate of 0.05 wm, and the vessel was stirred at a slow rate (20 rpm at the 2 liter scale). The fermenter was spiked with an EGTA solution adjusted to pH 6.15, to a final concentration of 2 g/L just prior to glucose exhaustion. At this same time sterile-filtered lactose solution was added to a final concentration of 4 to 8 g/L. Harvest time was then determined through in-process ultra performance liquid chromatography (UPLC) analysis, nominally around 48 to 80 hours. The harvest culture was then cooled to <20° C., and the cells were then removed by centrifugation and filtration. The supernatant was concentrated 10 to 30-fold by tangential flow filtration, using 10 kDa (cut-off) modified cellulose acetate UF membranes. The supernatant was then diafiltered with 4 to 5 washes using a buffer containing 50 mM MES, 500 mM $Na_2SO_4$, pH 5.8. The diafiltered retentate was then sterile filtered, and ready for purification.

Regarding upstream process improvements, historically the culture produces the maximum amount of pyolysin at 4 hr into stationary phase, which is when glucose exhaustion occurs. The organism then begins to produce proteases, however, which over time completely degrade the toxin. Thus, harvesting of the cells was typically done 3 to 4 hr post-glucose exhaustion, when the O.D. at 600 nm was typically ~3.7. The pH was then adjusted to 5.7 to 5.9 to further inhibit the proteases. One improvement in this process was the discovery that proteases were disabled with the addition of EGTA. Thus, adding EGTA prior to or at the time of glucose exhaustion allowed for the harvest of cells to coincide with maximum yield, as inactivation of the proteases, and subsequent feeding of the culture with a fresh carbon source, enabled the achievement of higher yields. Also, concentration of the supernatant was formerly done using 10 kDa PES ultrafiltration cassettes; the recovery of PLO was only about 65%. Changing over to 10 kDa modified cellulose acetate (e.g. Hydrosart) ultrafiltration cassettes, however, enabled the recovery of PLO to be improved to ~100%.

Further improvements to this process included phosphate buffering, the addition of a vitamin solution, as well as the addition of magnesium to the culture. Regarding phosphate buffering, 25 mM sodium phosphate at pH 6.8 was determined to be optimal. As for the vitamin solution, the following composition was added: Vitamin B12 (2.5 mg/L); myo-inositol (50 mg/L); uracil (50 mg/L); nicotinic acid (10 mg/L); calcium pantothenate (50 mg/L); pyridoxal-HCl (25 mg/L); pyridoxamine-2HCl (25 mg/L); riboflavin (50 mg/L); thiamine-HCl (25 mg/L); p-aminobenzoic acid (5 mg/L); biotin (5 mg/L); folic acid (20 mg/L); niacinamide (25 mg/L); and p-NAD (62.5 mg/L). Regarding the addition of magnesium, this could be supplied in the form of magnesium citrate, magnesium gluconate, or magnesium sulfate.

Further improvements to this process included batch and/or fed-batch fermentation strategies, using single or multiple carbon source supplementation. The carbon source can also contain additional nutritional factors and/or salts, such as hemin and phosphate. Planned fermentation optimisation strategies to maximise growth and production of pyolysin include controlling dissolved oxygen, redox, pH and carbon dioxide levels. The incubation temperature may also be improved, as some experimental work has indicated that a lower operating temperature may be beneficial.

With respect to downstream processing and purification of the pyolysin, the protein was purified via hydrophobic interaction chromatography (HIC) using a phenyl sepharose resin equilibrated with 50 mM MES, 500 mM Na2SO4, pH5.8; it was eluted in 50 mM MES pH5.8. The purified protein was then concentrated, followed by buffer exchange into phosphate buffer (sodium or potassium). Haemolytic activity was then determined, to ensure that active protein had been purified. This was done by serial dilution of the pyolysin with assay buffer, followed by incubation at 37° C. of pyolysin with horse red blood cells. This was then centrifuged to pellet the intact red blood cells, the soluble (lysed) material was transferred to a fresh plate, the O.D. at 405 nm was measured, and results were plotted. Haemolytic units (HU) were determined at the midpoint of the curve, and pyolysin was considered detoxified when haemolytic units were less than 1000 HU. UPLC and SDS-PAGE were then used to confirm the identity of the isolated protein. Finally, pyolysin was inactivated by treatment with 0.25-0.5% (v/v) formalin for 24-48 hr at 20° C., and then sterile filtered.

Example 2. Additional Improvements for Increasing the Expression Level of Pyolysin The raw materials required to prepare the Metritis Seed Medium are shown in Tables 1 and 2 (including target concentrations).

TABLE 1

Hemin Chloride Solution

| Number | Ingredient | Target Concentration |
|---|---|---|
| 1 | Hemin Chloride | 100 mg/L |
| 2 | 1M NaOH Solution | 10 mL/L |

TABLE 2

Metritis Seed Medium

| Number | Ingredient | Target Concentration |
|---|---|---|
| 1 | Polysorbate 80 | 1 g/L |
| 2 | Glucose | 2.75 g/L |
| 3 | Magnesium D-Gluconate Hydrate | 1.1 g/L |
| 4 | $NaH_2PO_4 \cdot 2H_2O$ | 3.588 g/L |
| 5 | $Na_2HPO_4$ | 10.934 g/L |
| 6 | Tryptone | 30 g/L |
| 7 | Yeast Extract | 15 g/L |
| 8 | Hemin Chloride Solution | 40 mL/L |

The hemin chloride solution is always prepared fresh on the day required. Hemin chloride powder is firstly dissolved in the appropriate volume of 1 M NaOH and when fully dissolved, made up to volume with distilled water.

Due to the high viscosity of polysorbate 80 it is easier to weigh this component directly into a glass beaker as the first step in preparing the Metritis Seed Medium. Add about 60% of the final volume of distilled water to the beaker with a magnetic stirrer and proceed to mix and heat the solution to about 50 to 60° C. Note that this solution will become cloudy when heated. Slowly add all of the other components in the order shown in Table 2. Fully dissolve all ingredients and make up to volume with distilled water. Heat sterilise the medium at 121° C. for 15 to 20 minutes. The medium has a shelf life of 7 days at room temperature. This short shelf life is due the hemin content. If a basal medium is prepared without hemin, this would extend the shelf life to about 3 months at room temperature. Filter sterilised hemin chloride solution could be added to portions of a bulk basal medium as required. However, for certain markets this will require extraneous agents testing of the material prior to use.

For all fermentation studies performed up to and including 35 L pilot-scale, only two seed stages have been necessary to provide sufficient inoculum volume.

The first stage can be grown into stationary phase and has a lot of flexibility in its incubation period. The second stage is used to "freshen up" the cells and is to be transferred to the fermentation stage in exponential growth.

Disposable Corning Erlenmeyer Flasks with smooth walls and vented caps have been used for all fermentation studies to date. However, other disposable or non-disposable culture flasks should be equally as good. For all seed stages, flasks have been filled to 32% of total volume and post inoculation, incubated in a $CO_2$ shaking incubator set to 5% and 100 rpm. A $CO_2$ incubator was first used due to greatly improved growth. However, a much better growth medium has since been developed, so a standard incubator may now be satisfactory (these studies have not been performed).

An experiment testing the maximum number of seed passages from the *T. pyogenes* Master Seed showed there was no detrimental effect on pyolysin yield. The experimental design was based on a theoretical final fermentation culture volume of 10,000 L, whereby 7 passages from the master would be sufficient for this scale-up process. This was based on preparing a working seed bank with a generous 3 passages from the master seed.

The experiment tested pyolysin productivity in a 35 L pilot fermenter inoculated with the $6^{th}$ passage from the master seed. The first 5 passages were 40 mL volumes in 125 mL flasks and the 6th seed stage was 320 mL in a 1000 mL flask.

Seed Stage 1 (125 mL—Scale Example)

Thaw and open *T. pyogenes* working seed ampoule aseptically. Inoculate 40 mL of Metritis Seed Medium in a 125 mL smooth-walled flask with 0.5% v/v of ampoule. Incubate aerobically 16-28 hours at 37° C. on a shaking platform at 100 rpm in a $CO_2$ incubator set at 5%. ODeoo should be between 3 and 7 and there should be no residual glucose remaining (refer Section 3.6.2). Culture should be tested for purity by streaking onto sheep or horse blood agar plates (refer Section 3.6.5).

Seed Stage 2 (125 mL—Scale Example)

Inoculate 40 mL of Metritis Seed Medium in a 125 mL smooth-walled flask with 10% v/v of Seed Stage 1 (SS1). Incubate aerobically 4-8 hours at 37° C. on a shaking platform at 100 rpm in a $CO_2$ incubator set at 5%. 00600 should be between 1 and 3 and ensure there is some residual glucose remaining (refer Section 3.6.2) in Seed Stage 2 (SS2) prior to inoculating the fermenter/s. Culture should be tested for purity by streaking onto sheep or horse blood agar plates (refer Section 3.6.5).

The raw materials required to prepare the Metritis Production Basal Medium are shown in Table 3.

TABLE 3

Metritis Production Basal Medium (including target concentrations)

| Number | Ingredient | Target Concentration |
|---|---|---|
| 1 | Polysorbate 80 | 1 g/L |
| 2 | Glucose | 0.5 g/L |
| 3 | Magnesium D-Gluconate Hydrate | 1.1 g/L |
| 4 | $NaH_2PO_4 \cdot 2H_2O$ | 3.588 g/L |
| 5 | $Na_2HPO_4$ | 10.934 g/L |
| 6 | Tryptone | 30 g/L |
| 7 | Yeast Extract | 15 g/L |

The general preparation of the Metritis Production Basal Medium is the same as that described above for the Metritis Seed Medium. The medium is similar, but has no hemin chloride addition and a lower glucose concentration. Heat sterilise the required volume of basal medium in fermenters at 121° C. for 30 to 60 minutes.

This medium supersedes a Tryptone Soya Broth (TSB)-based medium that was sensitive to high heat sterilising loads, whereby toxin yields were greatly reduced. This improved medium is much more heat tolerant, but the hemin was deliberately excluded from this developmental study to only compare tryptone with high (equivalent to TSB of about 2.5 g/L) and low (0.5 g/L) glucose concentrations versus TSB. The intention was to later compare the improved medium heat sterilised with and without hemin. This work has yet been performed.

After the Metritis Production Basal Medium has been heat sterilised in the fermenter/s and cooled, the Metritis Complete Production Medium is prepared by adding filter sterilised components 1 and 2 at the rates shown in Table 4. The residual glucose concentration of this medium should be 14±2 mM. The EGTA and lactose solutions are added approximately 10 to 12 hours post inoculation when residual glucose is less than 8 mM and 00600 is greater than 2.5 (refer sections 3.5.4 and 3.5.6, respectively). The lactose solution is added as either component number 4a or 4b, depending on whether bolus or continuous feeding strategies are employed.

TABLE 4

Metritis Complete Production Medium

| Number | Ingredient | Addition Rate (per Litre of Metritis Production Basal Medium) | Comments |
|---|---|---|---|
| 1 | Vitamin/Hemin Solution | 40 mL | |
| 2 | 50% Glucose Solution | 4 mL | |
| 3 | 100 g/L EGTA Solution pH 5.8 | 20 mL | Only add post inoculation when residual glucose <8 mM and $OD_{600}$ >2.5 |
| 4a | 50% Lactose Solution (For Bolus Additions ONLY) | 8 to 16 mL | Concentration used for single or multiple bolus additions. Currently added post EGTA addition |
| 4b | 6% Lactose Solution (For Fed-Batch Addition ONLY) | 70 to 140 mL | Concentration used for fed-batch addition. Currently added post EGTA addition |

Vitamin Stock Solution

The raw materials required to prepare the Vitamin Stock Solution are shown in Table 5. Combined vitamin $K_1$ and $K_2$ addition did show yield improvements in both flask and fermentation studies. These have not been included in the current vitamin stock solution, as further work is required to investigate whether this additional complexity is justified. It is not known whether only one or both of vitamins $K_1$ and $K_2$ are beneficial. Vitamins $K_1$ and $K_2$ are not water soluble and were dissolved in DMSO for the experiments performed.

TABLE 5

Vitamin Stock Solution (including target concentrations)

| Number | Ingredient | Target Concentration |
|---|---|---|
| 1 | Vitamin B12 | 2.5 mg/L |
| 2 | Uracil | 50 mg/L |
| 3 | Nicotinic Acid | 10 mg/L |
| 4 | Calcium Pantothenate | 50 mg/L |
| 5 | Pyridoxal•HCl | 25 mg/L |
| 6 | Pyridoxamine•2HCl | 25 mg/L |
| 7 | Riboflavin | 50 mg/L |
| 8 | Thiamine•HCl | 25 mg/L |
| 9 | p-Aminobenzoic Acid | 5 mg/L |
| 10 | Biotin | 5 mg/L |
| 11 | Folic Acid | 20 mg/L |
| 12 | Niacinamide | 25 mg/L |
| 13 | β-NAD | 62.5 mg/L |
| 14 | Myo—Inositol | 50 mg/L |

It is easier to prepare a non-sterile stock solution of vitamins that can be frozen at −20° C. and stored for up to 12 months. Add about 20 to 30% of the final volume of cold distilled water into a glass beaker, Schott Bottle or glass Erlenmeyer Flask (or any other suitable vessel) with a magnetic stirrer. Weigh each component one at a time and rinse into the vessel with cold distilled water with vigorous stirring. Make up to volume and ensure all ingredients are fully dissolved and then dispense as 40 mL non-sterile aliquots and freeze at −20° C. (or colder if desired).

Vitamin/Hemin Solution

It is possible to heat sterilise the hemin chloride component of the Metritis Production Basal Medium for 20 to 30 minutes without significantly affecting toxin yields. Further work is required to determine whether medium containing hemin chloride can be heat sterilised using higher heat loads without significantly affecting pyolysin yields. This will be an important part of the antigen manufacturing design to enable both robustness and establishing a global vaccine platform. Australia, for example, would only accept either a heat sterilised or gamma-irradiated hemin chloride addition (i.e. filter sterilised hemin chloride addition would not be acceptable to Australian regulatory authorities without extraneous agents testing). However, until this has been demonstrated experimentally, a filter sterilised Vitamin/Hemin Solution has been used as a medium additive post heat sterilisation. It is important to prepare this solution on the day of inoculating the fermenter/s due to its short shelf life. A combined hemin and vitamin solution was used to minimise volume increase in fermenters (otherwise 40 mL/L of both a hemin chloride and vitamin solution would be required). The raw materials required to prepare the Vitamin/Hemin Solution are shown in Table 6.

TABLE 6

Vitamin/Hemin Solution (including target concentrations)

| Number | Ingredient | Target Concentration |
|---|---|---|
| 1 | Hemin Chloride | 100 mg/L |
| 2 | 1M NaOH Solution | 10 mL/L |
| 3 | Vitamin Solution | 1 L/L |

The Vitamin/Hemin Solution is always prepared fresh on the day required. Thaw the required amount of vitamin stock solution and mix by shaking. Hemin chloride is firstly dissolved in the appropriate volume of 1 M NaOH and when fully dissolved, added to the required volume of non-sterile vitamin solution. This makes a slightly larger volume than the total required by the amount of NaOH added, but this 1% increase is negligible. Until the heat sterilisation effect on hemin in the basal medium is resolved this preparation method is satisfactory. If it is decided to remain with a filter sterilised HeminNitamin Solution, then this could be performed more accurately by preparing the vitamin stock solution at 95% of volume and then making up to volume after the hemin addition. Filter sterilise the solution and store at 2 to 8° C. until ready for use on the day of preparation.

TABLE 7

50% Glucose Solution (including target concentrations)

| Number | Ingredient | Target Concentration |
|---|---|---|
| 1 | Glucose | 500 g/L |

Bring about 50% of the final volume of distilled water close to the boil in a glass beaker covered in aluminium foil (or similar) with a magnetic stirrer. Slowly add the glucose powder and continue stirring while covered with heating (avoiding the solution to boil over) until fully dissolved. Make up to volume, allow to cool and filter sterilise.

TABLE 8

10% EGTA Solution pH 5.8 (including target concentrations)

| Number | Ingredient | Target Concentration |
|---|---|---|
| 1 | EGTA | 100 g/L |
| 2 | 30% NaOH | ~27 mL/L |
| 3 | 1M NaOH | N/A |

Add EGTA to about 60% of the final volume of cool distilled water in a glass beaker with a magnetic stirrer. With continual stirring measure the initial pH of the solution which will appear as a slurry at this stage. Rapidly add 80% of the total 30% w/v NaOH solution required with a target pH of 5.8 when fully dissolved. When nearly dissolved, slowly add the balance of 30% w/v NaOH required to achieve the target pH as well as achieving full dissolution. It is easy to overshoot the target pH at the very end of the preparation, so at this point it may be better to use 1 M NaOH for the final adjustment. If the pH target is slightly overshot, it can be adjusted back with a 2 M HCl solution (or similar). After accurately adjusting to a pH of 5.8, make up to volume and filter sterilise.

TABLE 9

| 50% Lactose Solution (including target concentrations) | | |
|---|---|---|
| Number | Ingredient | Target Concentration |
| 1 | Lactose | 500 g/L |

Bring about 50% of the final volume of distilled water close to the boil in a glass beaker covered in aluminium foil (or similar) with a magnetic stirrer. Slowly add the lactose powder and continue stirring while covered with heating (avoiding the solution to boil over) until fully dissolved. Make up to volume, allow to cool and filter sterilise.

TABLE 10

| 6% Lactose Solution (including target concentrations) | | |
|---|---|---|
| Number | Ingredient | Target Concentration |
| 1 | Lactose | 60 g/L |

Add lactose powder to approximately 80% of the final volume of distilled water in a beaker with a magnetic stirrer and mix until fully dissolved. Make up to volume and filter sterilise.

Fermentation Scalability

The *T. pyogenes* fermentation process has been successfully grown at 0.5, 2, 5 and 35 L scales. Usually the most challenging physicochemical property changes are observed when fermentation processes are scaled from laboratory to pilot-scale. However there were no problems observed during the scale-up to a 35 L pilot-scale with the process demonstrating good scalability all the way from small lab-scale fermenters. Based on the good process scalability observed so far, problems are not expected when scaling up to production vessels.

Table 11 summarises the key physical parameters of the fermenters tested.

TABLE 11

| Fermenter Physical Parameters | | | | |
|---|---|---|---|---|
| | 0.5 L | 2 L | 5 L | 35 L |
| Vessel Type | Glass | Glass | Glass | Stainless Steel |
| Controller | Sartorius DCU Biostat Q | Sartorius Biostat B-DCU II | Sartorius Biostat B-DCU II | Sartorius DCU Touch |
| Software Control | Sartorius MFCS Version 3.0 | Sartorius MFCS Version 3.0 | Sartorius MFCS Version 3.0 | Sartorius MFCS Version 3.0 |
| Vessel Height | 104 mm | 175 mm | 250 mm | 482 mm |
| Vessel Diameter | 85 mm | 130 mm | 160 mm | 305 mm |
| Vessel Aspect Ratio | 1.22:1 (at 0.5 L) | 1.35:1 (at 2 L) | 1.56:1 (at 5 L) | 1.58:1 (at 35 L) |
| Impeller Type and Number | 1 x Rushton 6 blade | 2 x Rushton 6 blade | 2 x Rushton 6 blade | 3 x Rushton 6 blade |
| Impeller Diameter | 49 mm | 53 mm | 62 mm | 101 mm |
| Vessel Volume | 0.67 L | 3 L | 6.6 L | 50 L |
| Working Volume | 0.45 to 0.5 L | 2 to 2.2 L | 4 to 5 L | 35 L |
| Sparger Type | Drilled Hole | Drilled Hole | Drilled Hole | Drilled Hole |
| Agitation | 70 rpm | 20 to 600 rpm | 50 rpm | 35 rpm |
| Number of Mass Flow Controllers per Vessel | 1 | 6 | 6 | 4 |
| Gases Required | Air, Nitrogen and Oxygen | Air, Nitrogen and Oxygen | Air, Nitrogen and Oxygen | Air, Nitrogen and Oxygen |
| Gas Flowrates | 0.03 to 0.2 vvm | 0.05 to 0.2 vvm | 0.03 to 0.2 vvm | 0.03 to 0.2 vvm |
| Number of Probe Ports | At least 3 | Only 3 | Only 3 | Only 3 |
| Redox Control Capable? | Available, but not tested | Installed and tested | Available, but not tested | Not available, can measure redox only |
| External Inputs Available? | Yes, 1 only per vessel | Yes, 2 per vessel | Yes, 2 per vessel | No |
| Number of Pumps Required | 1 x Base addition and 1 x Feed | 1 x Base addition and 1 x Feed | 1 x Base addition and 1 x Feed | 1 x Base addition and 1 x Feed |

Fermentation Strategy

Prior to inoculation, the starting operating conditions for the fermenters tested to date are shown in Table 12.

Table 12 Fermenter Initial Operating Parameters

TABLE 12

| Fermenter Initial Operating Parameters | | | | |
|---|---|---|---|---|
| | 0.5 L | 2 L | 5 L | 35 L |
| Temperature | 37° C. | 37° C. | 37° C. | 37° C. |
| Initial Stirrer Speed | 70 rpm | 45 rpm | 50 rpm | 35 rpm |
| $pO_2$ control using pure $O_2$ only | | | | |
| Setpoint | 5% | 5% | 5% | 5% |
| Deadband | Zero | Zero | Zero | Zero |
| XP | 5% | 5% | 5% | 5% |
| TI | 999 s | 5000 s | 5000 s | 999 s |
| TD | 10 s | 10 s | 10 s | 10 s |
| Max $O_2$ flow | 0.03 vvm | 0.05 vvm | 0.03 vvm | 0.03 vvm |
| Initial Air Flowrate | Off | Off | Off | Off |
| pH Start | 7.0 to 7.4 | 7.0 to 7.4 | 7.0 to 7.4 | 7.0 to 7.4 |
| pH Control Method | One-way base using 30 to 40% NaOH | One-way base using 30 to 40% NaOH | One-way base using 30 to 40% NaOH | One-way base using 30 to 40% NaOH |
| pH control | | | | |
| Setpoint | 6.15 | 6.15 | 6.15 | 6.15 |
| Deadband | Zero | Zero | Zero | Zero |
| XP | 15% | 15% | 15% | 15% |
| TI | 999 s | 1000 s | 1000 s | 999 s |
| TD | 0 s | 0 s | 0 s | 0 s |
| Redox Control | Not yet tested | −250 mV using algorithms | Not yet tested | Not yet tested |

Dissolved Oxygen Control and $CO_2$ Environment

The current strategy to produce the highest yields of pyolysin from *T. pyogenes* is to inoculate the Metritis Complete Production Medium in each fermenter with 0.5% of actively growing SS2 cells. Initial growth is commenced with a slow stirring rate and the use of pure oxygen on demand to maintain a dissolved oxygen setpoint of 5% with a maximum flowrate of 0.05 vvm. The concept behind this strategy is to allow the cells to rapidly grow, but also to minimise $CO_2$ being stripped from the liquid phase by gas bubbles. This is the reason for using oxygen instead of air. Problems with DO probes malfunctioning have occasionally caused issues using this strategy, so it may be equally as good to implement a continuous oxygen flowrate of 0.05 vvm up until the redox control phase.

Redox Control

The reason redox control is employed as part of the fermentation strategy for *T. pyogenes* is to accurately maintain the optimal microaerophillic environmental conditions to maximise pyolysin productivity. Although not technically correct, it is a method to control very low levels of dissolved oxygen that cannot be measured by a standard optical or polarographic dissolved oxygen probe. Redox control also assists in driving catabolic reactions important in both microaerophillic and aerobic cultures. The advantage of redox control is greatly improved process robustness whereby batch to batch variability of complex medium components (e.g. tryptone and yeast extract) are minimised by the system self-tuning to the optimal redox level. In a system without redox control, lower cell yields observed with a poor batch of tryptone would result in a sub-optimal microaerophillic condition causing lowered pyolysin yields. Redox control has the ability to automatically adjust the fermentation microaerophillic environment to the optimal level regardless of small variations in the quality of raw materials. The disadvantage of redox control is that redox probes cannot be calibrated but only their output checked against theoretical values of standard solutions. These values also have a fairly large error of about ±20 mV.

Redox control cannot be used immediately post inoculation as the system requires enough actively growing cells to generate a sufficiently large dissolved gaseous environment to provide the "momentum" needed to drive the redox lower than the control setpoint. This is the reason p02 control is used for the initial growth phase of the fermentation.

The current redox control strategy was designed using changes in stirrer speed at a fixed air sparging rate to increase redox, and reducing the air sparging rate to decrease redox. Air was used instead of oxygen with an effort to entirely remove the need to use any pure oxygen in the final GMS fermentation method. The disadvantage of using air is that the optimal dissolved $CO_2$ concentration to maximise pyolysin yields may not be possible with the heightened gas bubbling rate.

Currently an algorithm is being used to control redox (refer Appendix 2). This type of algorithm can be improved in its level of sophistication and ability to self-tune, however, if a decision is made to progress with redox control into the final manufacturing process, more robust alternatives are available. One solution maybe to have the appropriate fermenter vendor custom make a cascade PID control system similar to that already installed for $pO_2$ control whereby the control could also cascade through stirrer, air and oxygen sparging. Alternatively there are customised redox control fermenters available that control redox by passing an electrical current through the culture.

$CO_2$ Control

A strategy has not yet been tested to control $CO_2$. However, it is believed that controlling the dissolved $CO_2$ concentration may assist in both optimising and maintaining consistency in pyolysin yields. Whilst testing the redox control strategy with a Mettler Toledo InPro5000i dissolved $CO_2$ probe in situ, it was clearly observed that higher gas sparging flowrates had a significant effect on dissolved $CO_2$ concentrations. Stirrer speed appeared to have a minimal effect on $CO_2$ levels.

The redox control algorithm could also be used to control dissolved $CO_2$. A complementary algorithm written could increase or decrease gas sparging flowrates as required to control an output from a dissolved $CO_2$ probe or other $CO_2$ measurement device (e.g. off gas measurement). This could also be performed from a separate mass flow controller so that redox and $CO_2$ control are independent of one another. This concept has been manually tested and does work, although some effort is required to determine, firstly whether or not dissolved $CO_2$ concentration is important for optimising pyolysin yields and if it is found to be important, then what is the optimal control level.

If dissolved $CO_2$ is found to be important in optimising pyolysin yields, then it will probably be easier to control the optimal level using pure oxygen sparging rather than air, due to the finer control enabled through the lower gas flowrate required.

Protease Inhibition

Twenty millilitres of 10% EGTA Solution (pH 5.8) should be added per litre of culture when the residual glucose concentration is below 8 mM and the OD600 is greater than 2.5. If the initial glucose concentration is in the correct starting range of 14±2 mM, then the timing of EGTA addition is about 10 to 12 hours post inoculation. This is a critical part of the fermentation strategy, and must be closely monitored and carefully performed. Although EGTA chelates many divalent metal ions, it has a very high affinity for $Ca^{2+}$ ions. The reason EGTA is added to the culture is to inhibit the activity (and possibly formation) of proteases. We have demonstrated that calcium is the main metal implicated in protease activity in *T. pyogenes* cultures. When extra calcium is added to flasks with the normal amount of EGTA, pyolysin concentrations rapidly reduce, yet magnesium addition improved yields.

Lactose

It is important to add the lactose solution prior to glucose exhaustion so that growth is not stalled, but the strategy employed has been to add lactose to the culture post-EGTA addition. It could be added to the culture pre-inoculation, but the only reason to add it post-EGTA addition is to enable accurate residual glucose monitoring for the far more critical EGTA addition step. If it is possible to monitor glucose concentration in the presence of lactose, then this methodology could easily be changed without any detrimental effect on yield.

Several studies have been performed using both batch and fed-batch lactose feeding. At this time it is not known whether a fed-batch strategy provides any benefit over single or several bolus additions of lactose. Bolus additions have been performed using 50% lactose solution additions. Due to the very low feed rate required a 6% lactose solution has been used for fed-batch fermentations to enable the use of peristaltic pumps at a 2 L working volume. A disadvantage of this method is the higher dilution effect. A more concentrated solution could be added using higher accuracy pumping methods (e.g. syringe pumps). Alternatively, if benefits are observed using a fed-batch strategy, then other nutrients and/or ingredients could be added to the feed (e.g. tryptone, magnesium, hemin chloride, etc.).

Magnesium

A small flask study was performed using various magnesium sources. Inorganic magnesium sulphate was compared in equimolar magnesium concentrations to three organic magnesium sources (magnesium gluconate, magnesium citrate and chlorophyll). Magnesium gluconate provided the highest pyolysin yields, however if this raw material is difficult to source then optimisation studies could easily be performed using other magnesium sources already available. The concept behind testing organic magnesium sources is that EGTA should be less able to sequester magnesium that is more tightly bound than with the weak ionic bonds of inorganic sources. There was concern that simply adding higher levels of inorganic magnesium may allow greater protease production (although this may be unfounded). Since magnesium is required for growth, the increased cell mass observed with magnesium addition should result in higher pyolysin yields (as observed in this flask study).

In-Process Analytical Methods

Optical Density

Cell growth is determined by changes in optical density measured at 600 nm in a spectrophotometer. Water is generally used as the diluent when values exceed 0.5 to ensure samples are maintained within the linear range of absorbance measurement accuracy. Using the production growth medium provides a slight improvement in accuracy such that background absorbance is deducted. This is generally not deemed necessary as it only really affects results of the early stage of the culture growth phase.

Residual Glucose

Residual glucose is measured using a commercially available, hand-held blood glucose analyser. After inserting the testing strip into the device and waiting for an indication it is ready for a sample, about 10 to 20 μL of unfiltered fermentation culture is placed on the tip of the test strip and a result is provided in millimoles per litre.

Residual Lactose

The same analyser used for residual glucose also gives a result for residual lactose. The actual value provided is not accurate, but it still enables monitoring of relative residual lactose levels satisfactory for fermentation monitoring. However, it has been observed that growth significantly slows when residual lactose levels fall below 3 mM using this instrument. For both bolus and fed-batch lactose feeding, it is necessary to maintain a residual lactose concentration greater than 3 mM.

Pyolysin Concentration

The main in-process analytical technique used to measure pyolysin concentrations is reverse phase liquid chromatography using a UPLC. The other highly sensitive technique is a haemolysis assay that measures pyolysin concentration by assigning an arbitrary haemolysis unit to a crude standard and then measures other samples by referencing to this standard. This assay is very useful in measuring inactivation levels in pyolysin toxoid samples. Due to its high sensitivity, dilution errors are magnified for pyolysin samples with high concentrations (above ~50 μg/mL) making the assay quite variable unless extreme care is taken.

Purity Testing

Culture purity can be tested by streaking onto sheep or horse blood agar plates (SBA or HBA). Incubate plates aerobically for 48 to 96 hours at 37° C. Incubation in a $CO_2$ environment increases the growth rate. A pure culture will appear as small white/cream, convex, shiny colonies. Plates can also be incubated, however *T. pyogenes* colonies will also grow (although more slowly) under these conditions. Contamination is identified by observing other colony types on the plates.

Harvest and Cell Removal

The time of harvest is currently not well defined, but is commenced when the pyolysin concentration stops increasing in late stationary phase at about 60 to 70 hours post inoculation.

Culture harvest and cell removal at both research and development scales have been performed by cooling the culture to less than 20° C., aseptically harvesting and centrifuging in pre-sterilised centrifuge pots at 6,000×g for 15 to 30 minutes at 4° C. The supernatant is then aseptically decanted into a suitable sterile vessel and filter sterilised through a low protein binding sterilising grade filter. Cellulose acetate membranes have been the first choice due to their very low protein binding property. Sartorius Sartobran filters have generally been used with an appropriate filter membrane area chosen to suit the volume being filtered. For example, a 500 $cm^2$ Sartorius Sartobran P has sufficient capacity to filter at least 5 L of culture supernatant. These filters have a 0.45 μm pre-filter and 0.2 μm sterilising filter, but the supernatant is not difficult to filter, where other vendor equivalents should be equally suitable.

Concentration and Diafiltration

Product concentration has been performed using a Sartorius Alpha tangential flow filtration device with both Sartorius 10 kDa Hydrosart (modified cellulose acetate) and 10 kDa PES (polyether sulfone) Sartocon Slice cassettes as a non-sterile process. The Hydrosart cassettes demonstrated superior performance to the PES cassettes with 100% recovery compared to only about 70% for PES. This result is based on a limited number of processing runs, where more rigorous experimental testing is required to carefully compare membrane performances.

Prior to commencing concentration, the initial supernatant volume is carefully measured in a glass measuring cylinder, dispensed into the tangential flow filtration device and then conditioned across the membrane/s by circulating for 10 minutes with the permeate line closed. Following this initial set up, all ultrafiltration processing was performed with feed, retentate and permeate pressures maintained at 1.5, 0.5 and zero bar, respectively and the product temperature maintained at 15±2° C. The pyolysin crude supernatant is generally concentrated about 10-fold and then diafiltered 4 to 5 times with 50 mM MES/500 mM Na2SO4, pH 5.8 (the purification starting buffer). At the conclusion of the concentration and diafiltration steps, the system is carefully drained to minimise product foaming which can reduce recovery rates. The product volume is then measured in a glass measuring cylinder to accurately calculate the final concentration. The product is then filter sterilised through a cellulose acetate sterilising filter (generally a Sartorius Sartobran filter), and if not purified immediately, then aliquotted into suitable volumes (usually 100 to 250 mL) and frozen at −70° C. until ready for purification.

Example 3. Further Improvements for Increasing the Expression Level of Pyolysin Prior to the evaluation of various raw materials in the media, further refinements to the fermentation parameters were made. Regarding control parameters, it was determined that for bench scale development work, a redox control strategy using 02 sparging, limited to 0.1 vvm with agitation, but increasing if needed to hold the redox set point, was optimal. The redox set point used for development work was −447 mV. Further work to establish the redox (mv) range, and potential other methods of oxygen and agitation control, will be conducted.

With respect to fermentation control parameters, the starting pH of the culture was 7.2, and was allowed to drop to a pH of 6.15 during the fermentation process, where it was then maintained. Further work to establish pH control range and constant pH control will be conducted. During the initial fermentation growth phase, the dissolved oxygen (D.O.) was maintained at 5%, with an oxygen sparge limited to 0.1 wm; agitation was limited as well. When the target optical density (600 nm) of the culture reached at least 2.5, the culture was fed lactose to a final concentration of 30 g/L, and EGTA to a final concentration of 2 g/L. At this time, the control was switched from the D.O. set-point to the redox control program, for continued growth and the toxin production phase of the fermentation. The toxin production phase was continued for 30-70 additional hours, in order to harvest at the peak time of pyolysin production.

With these improved parameters in place, the evaluation of various raw materials in the media was performed, in order to determine whether existing manufacturing-approved sources would be suitable. Following multiple fermentation runs, it was concluded that vegetable-based polysorbate 80, instead of animal-based polysorbate 80, would be used. It was also determined that yeast extract sourced from Becton Dickinson was preferred, titrated at a concentration of 5 grams/liter. It was also determined that Oxoidm tryptone would be used.

Figure 2:
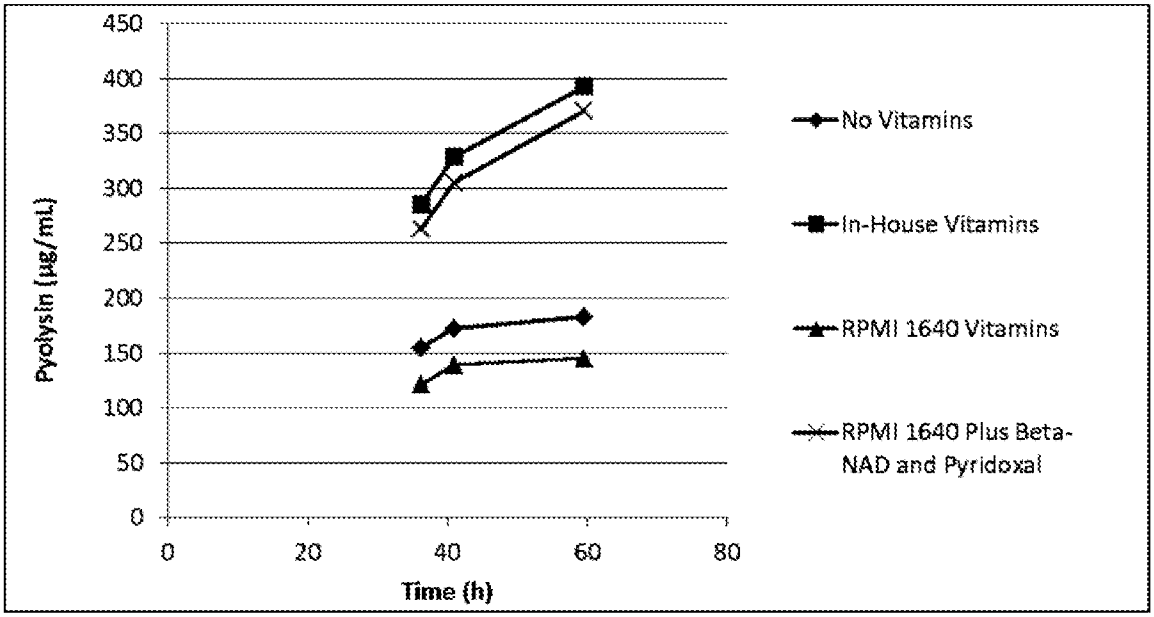
FIG. 2 is a comparison of the level of pyolysin production by *Trueperella pyogenes* in medium which contains no vitamins, an in-house vitamin solution, or a commercial vitamin solution supplemented with β-NAD and pyridoxal.
Figure 3:
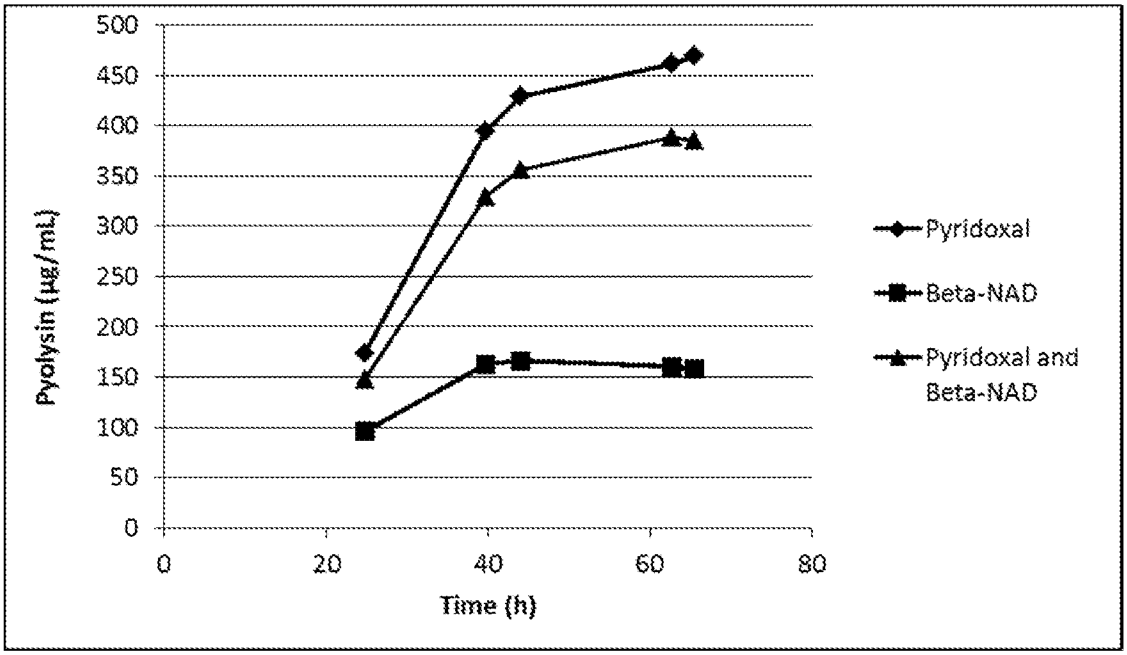
FIG. 3 is a comparison of the level of pyolysin production by *Trueperella pyogenes* in medium which contains β-NAD, pyridoxal, or both.
Figure 4:
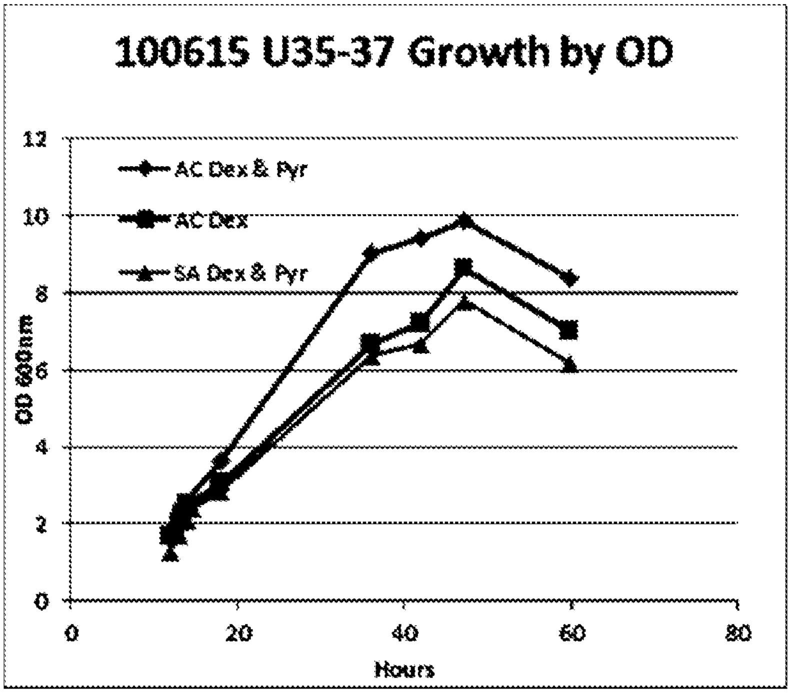
FIG. 4 is a comparison of the O.D. (600 nm) of *Trueperella pyogenes* in medium which contains pyridoxal (Pyr) which has either been autoclaved (AC) or sterilely added (SA) in combination with dextrose (Dex).
Figure 5:
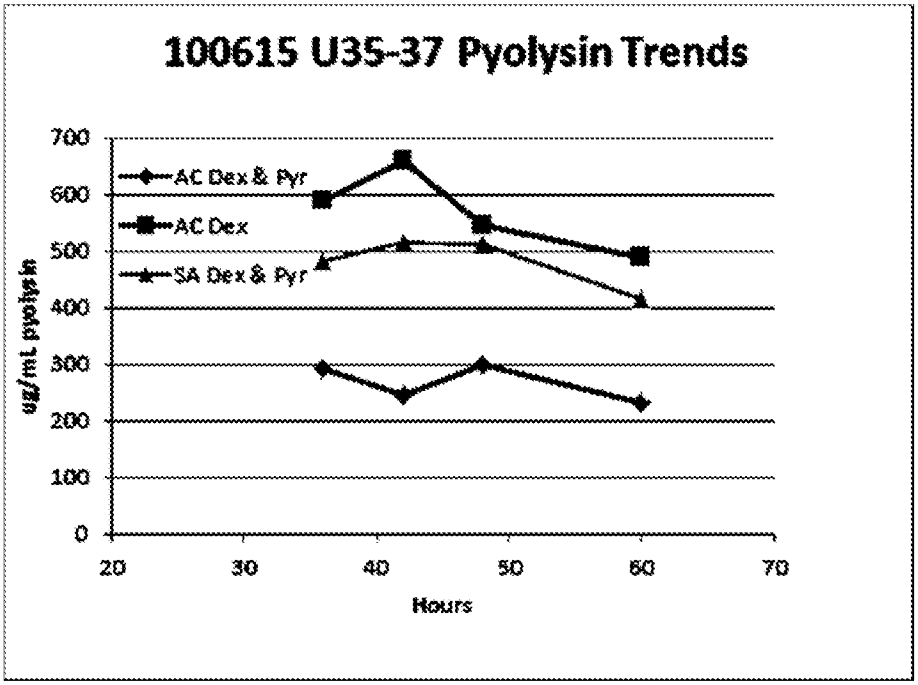
FIG. 5 is a comparison of the level of pyolysin production by *Trueperella pyogenes* in medium which contains pyridoxal (Pyr) that has either been autoclaved (AC) or sterilely added (SA) in combination with dextrose (Dex).

Previously, the vitamin solution added to the fermentation culture to increase the yield of pyolysin was prepared in-house. In an effort to simplify the fermentation process, it was thought that purchasing a commercially-available vitamin solution would be useful. A pre-mixed vitamin solution from Sigma, "RPMI 1640", was chosen, due to it being the closest match to the in-house vitamin preparation. An experiment was designed to test the pyolysin yield using RPMI 1640 vitamins versus the in-house vitamins in 2 L fermenters. The results of that experiment, shown in FIG. 1, demonstrated that the RPMI 1640 vitamin solution performed poorly in comparison to the in-house vitamin solution. Four components that were present in the in-house vitamin solution were not included in the RPMI 1640 vitamin solution (p-NAD, pyridoxal, uracil and nicotinic acid). Since uracil and nicotinic acid were shown not to be consumed during fermentation (data not shown), either lack of β-NAD and/or pyridoxal were thought to be the most likely cause of the reduced performance. An experiment was designed to test the hypothesis that the addition of β-NAD and/or pyridoxal supplementation of RPMI 1640 vitamins may increase the performance of this vitamin solution. As shown in FIG. 2, pyolysin yield was similar between the in-house vitamin solution and the supplemented RPMI 1640 vitamin solution. A further experiment was designed to test whether β-NAD and/or pyridoxal may be the only vitamin components required to supplement the culture medium. The results of this experiment (FIG. 3) confirmed that pyridoxal was the only vitamin required to be supplemented into the culture medium to increase the yield of pyolysin. As for when pyridoxal is added to the media, it must be done so as a sterile solution post-heat sterilization, however, as autoclaving it, while not affecting the O.D. of the culture (FIG. 4), did lead to a decrease in the level of pyolysin production (FIG. 5).

Figure 6:
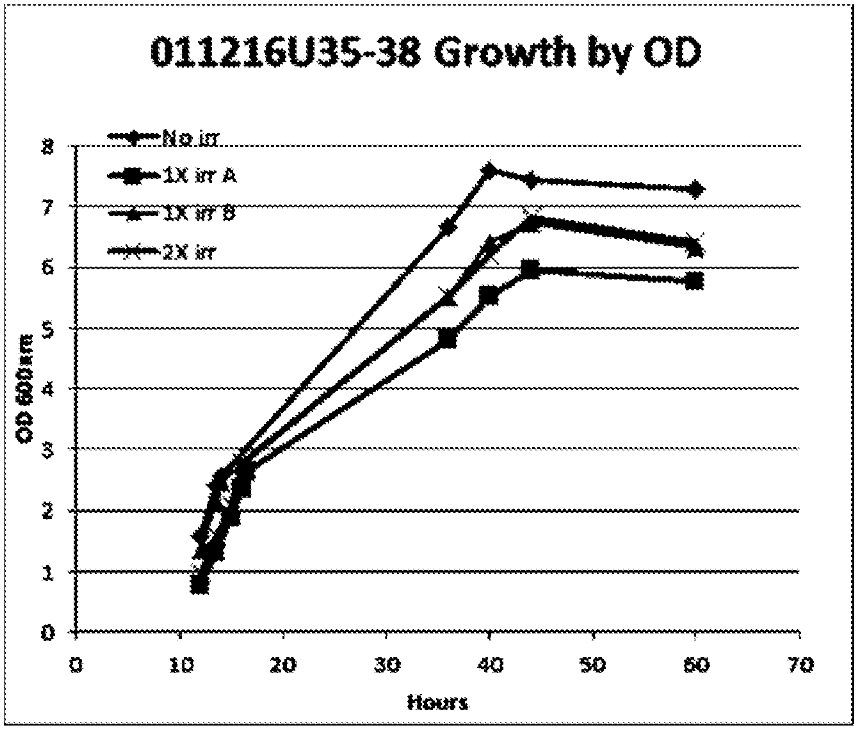
FIG. 6 is a comparison of the O.D. (600 nm) of *Trueperella pyogenes* in medium which contains hemin that has been irradiated for various lengths of time, or not irradiated at all.
Figure 7:
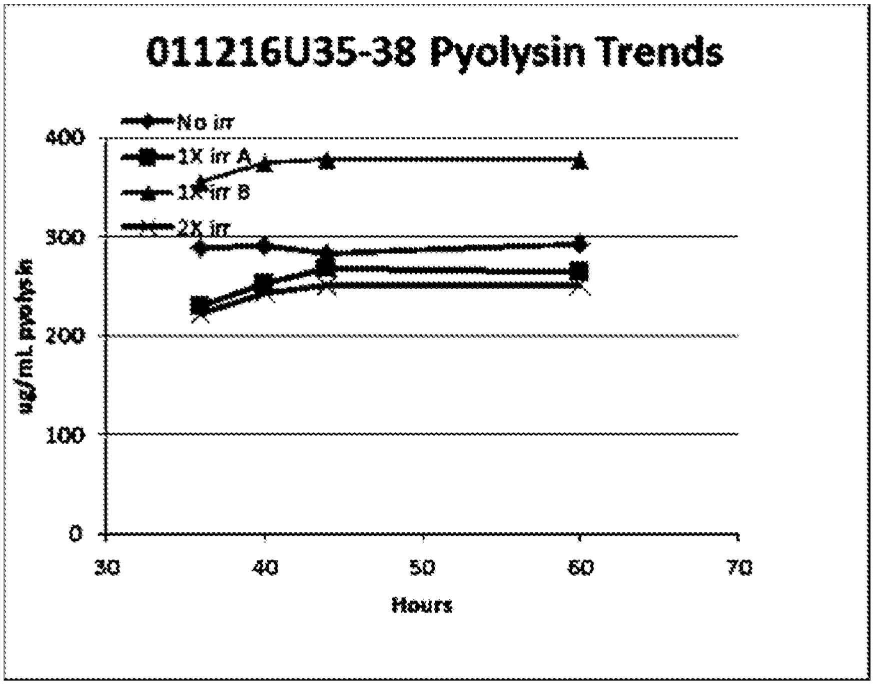
FIG. 7 is a comparison of the level of pyolysin production by *Trueperella pyogenes* in medium which contains hemin that has been irradiated for various lengths of time, or not irradiated at all.
Figure 8:
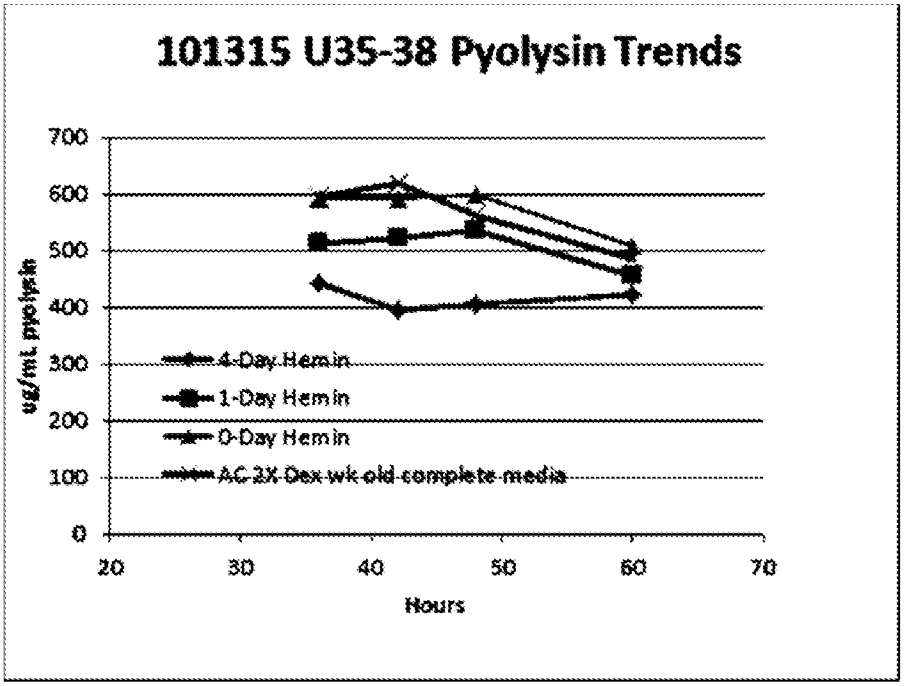
FIG. 8 is a comparison of the level of pyolysin production by *Trueperella pyogenes* in medium which contains hemin that has been held for various lengths of time prior to adding to the medium.

With respect to the hemin utilized in the media, it was determined that irradiation of the powdered raw material did not appear to have a direct effect on either the O.D. of the culture or the level of pyolysin production, as shown in FIG. 6 and FIG. 7. FIG. 8 demonstrates that pyolysin production decreases as the shelf life of the hemin solution increases; thus, the hemin was added immediately prior to heat sterilization.

Figure 9:
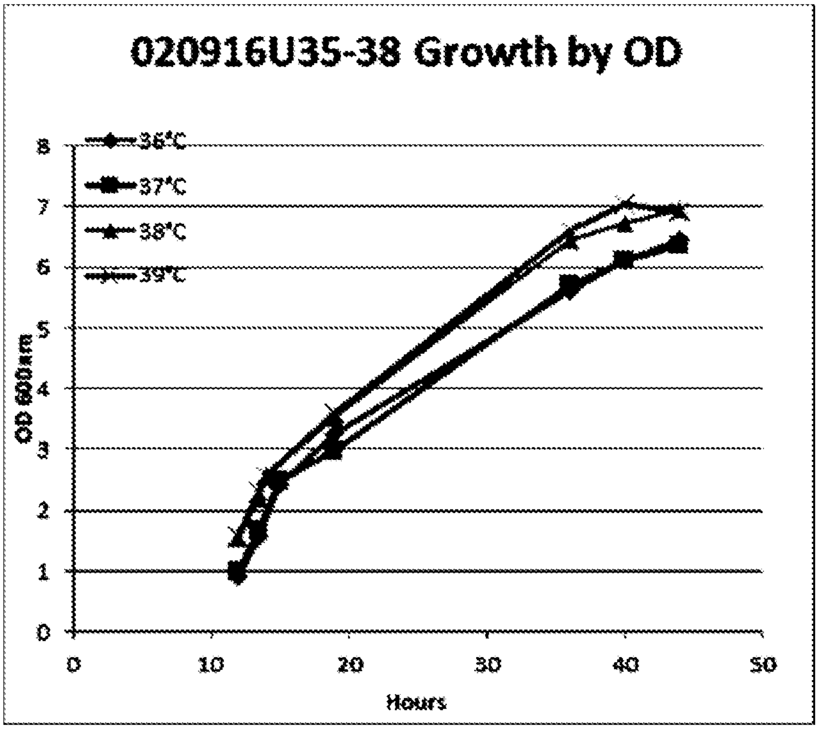
FIGS. 9 and 11 are comparisons of the O.D. (600 nm) of *Trueperella pyogenes* in medium which has been maintained at various temperatures.
Figure 10:
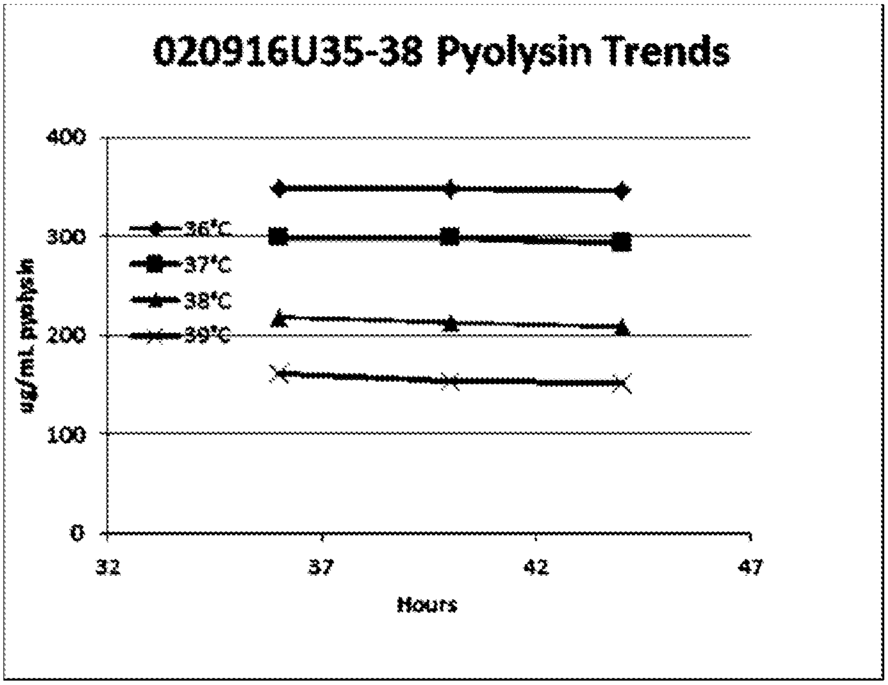
FIGS. 10 and 12 are comparisons of the level of pyolysin production by *Trueperella pyogenes* in medium which has been maintained at various temperatures.
Figure 11:
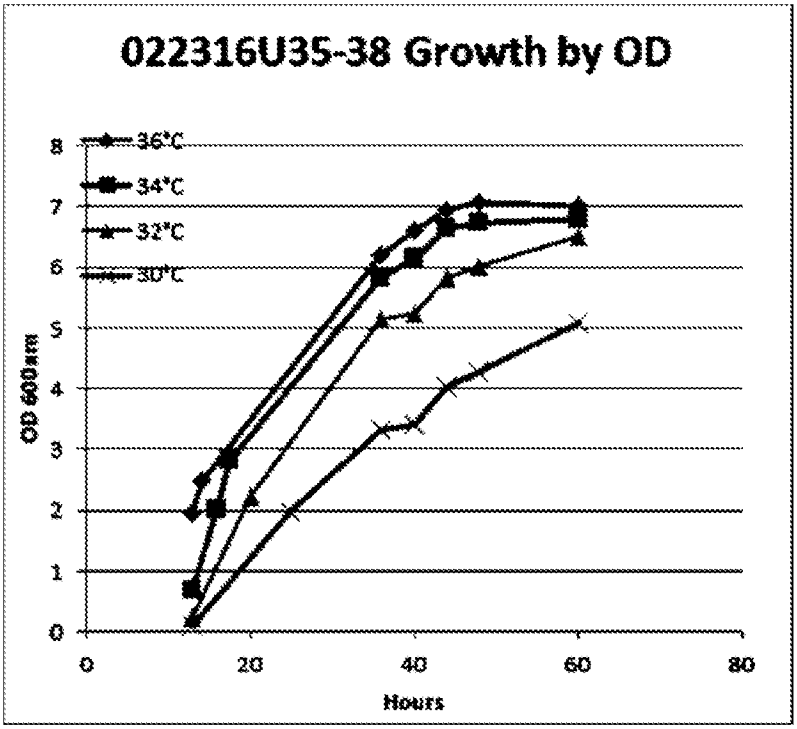
Figure 12:
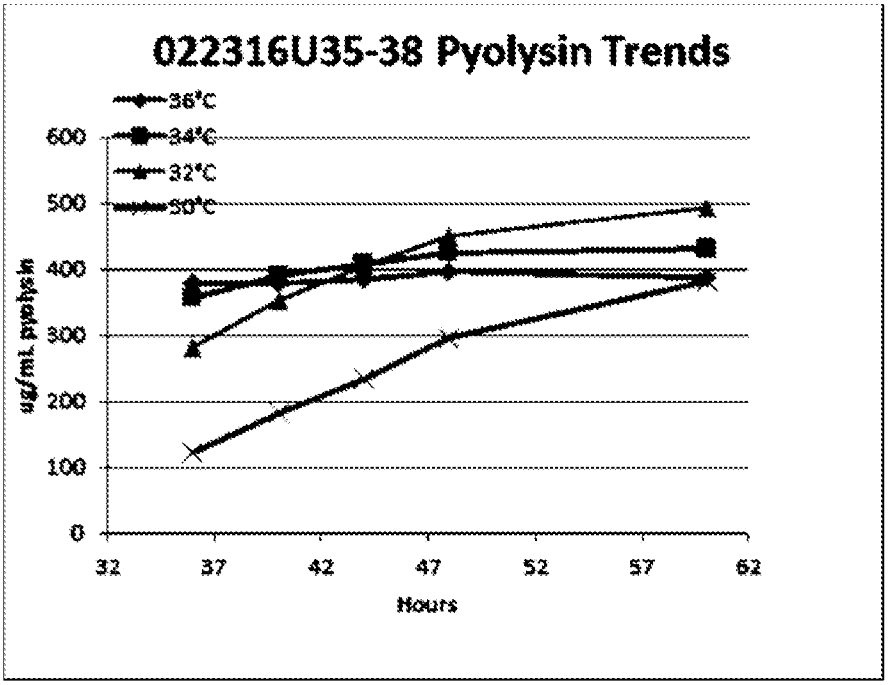
Figure 13:
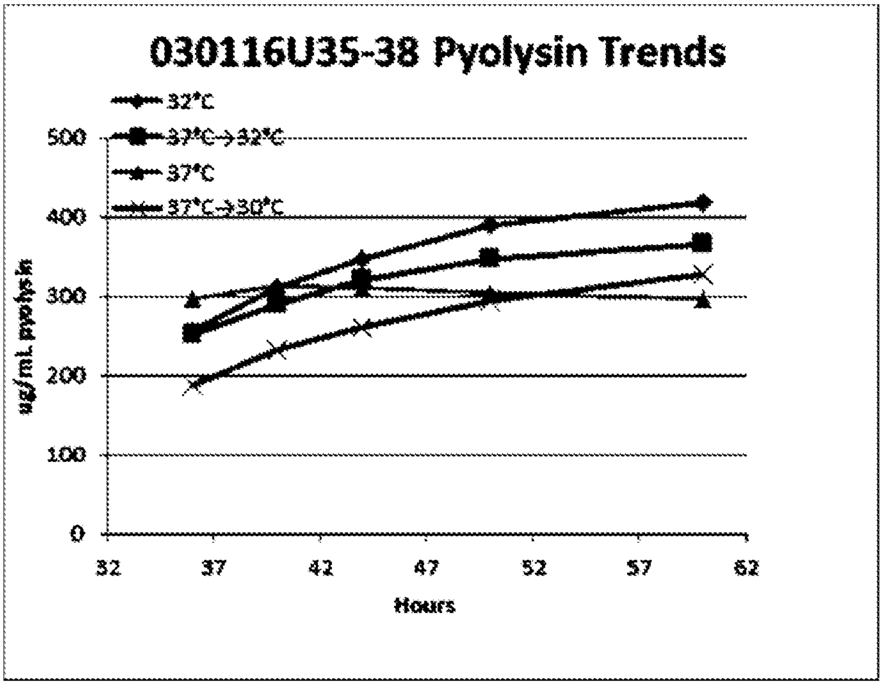
FIG. 13 is a comparison of the level of pyolysin production by *Trueperella pyogenes* where the temperature of the medium has been either maintained at 32° C., or shifted from 37° C. to 32° C., during the fermentation process.

In addition to the various media components, further investigations regarding the temperature at which the fermentation occurred took place. Previously, fermentations were carried out at 37° C. Subsequent experiments, however, indicated that a lower set point of 36° C. (versus the higher temperatures), while not having a significant effect on the O.D. of the culture (FIG. 9), did result in an increase in the amount of pyolysin produced (FIG. 10). The question was then raised as to what effect an even lower temperature might have on the level of pyolysin production. The result of these experiments lead to the conclusion that while lower temperatures lead to a decrease in the O.D. of the culture (FIG. 11), they also lead to an increase in the level of pyolysin produced, with the current optimal temperature being 32° C. (FIG. 12). As to whether maintaining the temperature of the culture at 32° C., or shifting it from 37° C. to 32° C. during the fermentation process, results in better yields of pyolysin, it was determined that constant temperature was better than shifting (FIG. 13).

Example 4. Further Improvements to the Pyolysin Purification Process

Concentration of the clarified fermentation harvest was performed by using 10 kDa polysulfone hollow fiber cartridges, with >95% recovery of pyolysin. Following concentration, a solution of 50 mM MES, 1.2 M Na2SO4, pH 5.8, was added to the concentrate to achieve a final concentration of 0.425 M sodium sulfate. The Na2SO4-treated material is filtered prior to application to the chromatography column.

The pyolysin was purified via hydrophobic interaction chromatography (HIC) using a phenyl sepharose resin equilibrated with 50 mM MES, 425 mM Na2SO4, pH5.8. Pyolysin was loaded to the column at a concentration from 1 G pyolysin/Liter of resin up to 12 G pyolysin/Liter of resin. It was then eluted in 50 mM MES pH5.8, with pyolysin yield >80%. The purified protein was then concentrated, followed by buffer exchange into phosphate buffer (sodium or potassium). Haemolytic activity was then determined, to ensure that active protein had been purified. This was done by serial dilution of the pyolysin with assay buffer, followed by incubation at 37° C. of pyolysin with horse red blood cells. This was then centrifuged to pellet the intact red blood cells, the soluble (lysed) material was transferred to a fresh plate, the O.D. at 405 nm was measured, and results were plotted. Haemolytic units were determined at the midpoint of the curve, and pyolysin was considered detoxified when haemolytic units were under 1000. UPLC and SDS-PAGE were then used to confirm the identity of the isolated protein. Finally, pyolysin was inactivated by treatment with 0.10% to 0.5% (v/v) formalin for 20-48 hr at 20° C., and then sterile filtered.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only, with the true scope and spirit of the invention indicated by the following claims.

The invention claimed is:

1. A method for increasing the yield of pyolysin produced by *Trueperella pyogenes*, wherein the method comprises: A) culturing *T. pyogenes* at 21 to 36 degrees C. in a basal medium that contains glucose, and, optionally, an additional concentrated carbon source selected from the group consisting of glucose, galactose, sucrose, maltose, oligosaccharides, glycerol, lactose, dextran, dextrin, mono methyl succinate, and N-acetal glucosamine; B) adding a calcium chelating agent and lactose to the culture medium prior to the exhaustion of glucose in the medium; C) harvesting *T. pyogenes*, and D) isolating pyolysin.

2. The method of claim 1, wherein the additional concentrated carbon source is lactose.

3. The method of claim 1, wherein the chelating agent is ethylene glycol tetraacetic acid (EGTA), ethylenediaminetetraacetic acid (EDTA), or a combination of the two.

4. The method of claim 3, wherein the chelating agent is EGTA.

5. The method of claim 1, wherein *T. pyogenes* replicates to a bacterial cell density higher than an optical density (O.D.) of 5 at 600 nm.

6. The method of claim 1, wherein the medium is maintained at a temperature between 21-36° C.

7. The method of claim 6, wherein the medium is maintained at a temperature between 28-32° C.

8. The method of claim 1, further comprising the use of the basal medium, wherein the Ph of the medium is between 6.0 and 8.0.

9. The method of claim 1, further comprising the use of the basal medium, wherein the medium comprises hemin as an iron source.

10. The method of claim 1, further comprising the use of the basal medium comprising Polysorbate 80 (Tween 80).

11. The method of claim 1, further comprising the use of the basal medium comprising a vitamin solution.

12. The method of claim 11, wherein the vitamin solution comprises one or more of the following: Vitamin B12; myo-inositol; uracil nucleobase; nicotinic add; calcium pantothenate; pyridoxal-HCl; pyridoxamine-2HCl; riboflavin; thiamine-HCl; p-aminobenzoic add; biotin; folic add; niacinamide; and □-NAD.

13. The method of claim 11, wherein the vitamin solution comprises pyridoxal-HCl.

14. The method of claim 1, further comprising allowing the culture Ph to decrease from the initial basal medium starting Ph to a level between 5.50 and 6.50, and then controlling the Ph between 5.50 and 6.50 by automatic addition of a basic titrant.

15. The method of claim 1, further comprising separating *T. pyogenes* proteases from the pyolysin.

16. The method of claim 15, wherein the separation of *T. pyogenes* proteases from pyolysin is achieved by a chromatography step.

* * * * *